United States Patent [19]

Furutachi et al.

[11] Patent Number: 4,594,313
[45] Date of Patent: Jun. 10, 1986

[54] COLOR IMAGE FORMING PROCESS COMPRISING BLOCKED MAGENTA DYE FORMING COUPLER

[75] Inventors: Nobuo Furutachi; Yoshinobu Yoshida, both of Kanagawa, Japan

[73] Assignee: Fuji Photo Film Co., Ltd., Kanagawa, Japan

[21] Appl. No.: 710,891

[22] Filed: Mar. 12, 1985

[30] Foreign Application Priority Data

Mar. 12, 1984 [JP] Japan ................................. 59-46874

[51] Int. Cl.⁴ .................... G03C 7/00; G03C 1/08; G03C 7/16; G03C 7/32
[52] U.S. Cl. ........................... 430/381; 430/387; 430/553; 430/555; 430/557; 430/558; 430/955
[58] Field of Search ............... 430/553, 555, 557, 558, 430/955, 387, 381

[56] References Cited

U.S. PATENT DOCUMENTS

| | | | |
|---|---|---|---|
| 4,076,533 | 2/1978 | Ota et al. ............... | 430/387 |
| 4,283,472 | 8/1981 | Gompf et al. ............ | 430/555 X |
| 4,304,845 | 12/1981 | Fujimatsu et al. ........ | 430/557 X |
| 4,310,618 | 1/1982 | Fernandez et al. ....... | 430/387 X |
| 4,338,393 | 7/1982 | Bailey et al. ........... | 430/558 X |
| 4,477,563 | 10/1984 | Ichijima et al. .......... | 430/553 X |

FOREIGN PATENT DOCUMENTS

| | | | |
|---|---|---|---|
| 0058922 | 5/1977 | Japan ................... | 430/553 |
| 0111034 | 7/1983 | Japan ................... | 430/554 |

OTHER PUBLICATIONS

"Blocked Dye-Forming Couplers" Research Disclosure, Jul. 1981, #20714.
"Blocked Pyrazolone Magenta Dye-Forming Coupler" Research Disclosure, Jul. 1980, #19536.

*Primary Examiner*—John Kittle
*Assistant Examiner*—Mukund J. Shah
*Attorney, Agent, or Firm*—Sughrue, Mion, Zinn, Macpeak, and Seas

[57] ABSTRACT

A color image forming process which comprises developing a silver halide photographic material using an aromatic primary amine developing agent in the presence of a blocked magenta image forming coupler represented by the following general formula (I):

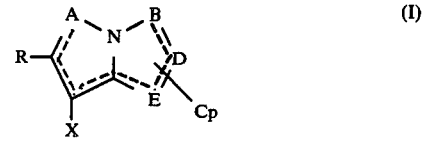

wherein R represents a hydrogen atom or a substituent; X represents a hydrogen atom, a halogen atom, a carboxy group or a coupling releasable group; Cp represents a coupling block group capable of forming a colorless or alkali-soluble product by reaction with the oxidation product of a color developing agent; A represents

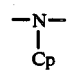

when Cp is bonded and —N= when Cp is not bonded; B and E each represents

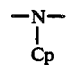

when Cp is bonded and —N= or

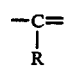

when Cp is not bonded; D represents —N= or

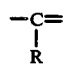

(wherein R has the same significance as defined above and said Rs in said D and B and E may be the same or different); and ------- represents three movable double bonds; said Cp is nit, however, bonded to E when A, D and E simultaneously contain a nitrogen atom and B contains a carbon atom; said coupler may form a dimer or more oligomers at R or X; and said substituent Rs on adjacent carbon atoms may form a ring with each other. The color image forming process uses a blocked magenta color image forming coupler having high coloring speed and maximum coloring density and excellent stability.

12 Claims, No Drawings

COLOR IMAGE FORMING PROCESS COMPRISING BLOCKED MAGENTA DYE FORMING COUPLER

FIELD OF THE INVENTION

This invention relates to a color image forming process for forming a novel magenta color image by a coupling reaction with the oxidation product of an aromatic primary amine oxidized by silver halide. More particularly, the invention relates to a color image forming process using a blocked magenta color image forming coupler having high coloring speed and maximum coloring density, and excellent stability.

BACKGROUND OF THE INVENTION

Hitherto, as magenta color image forming couplers, there are known 5-pyrazolones (as described in, for example, U.S. Pat. Nos. 2,343,703, 2,369,489, 2,600,788, 2,908,573, 3,062,653, 3,519,429, 4,080,211, etc.), pyrazolobenzimidazoles (as described in, for example, British Patent No. 1,047,612, etc.), indazolones (as described in, for example, U.S. Pat. No. 3,770,447, etc ), and pyrazolo [5,1-C][1,2,4]-triazoles (as described in, for example, U.S. Pat. No. 3,725,067, etc.).

Also, various kinds of so-called 2-equivalent couplers that a so-called coupling off group, i.e., a group capable of being released by causing a reaction with the oxidation product of an aromatic primary amino color developing agent is bonded to the coupling active position of the skeleton of each of the foregoing couplers for reducing the amount of silver used and controlling the coupling rate have been proposed (as described in, for example, U.S. Pat. Nos. 3,227,554, 3,311,476, 3,419,391, 3,926,631, 4,241,168, 4,076,533, 4,146,396, 4,237,217 and 4,351,897, Japanese Patent Publication No. 34044/78, etc.).

Also, recently, magenta color image forming couplers having a blocking group bonded to the oxygen atom of an enol in the state that the 5-position of 5-pyrazolone is enolated at the position capable of reacting with the oxidation product of an aromatic primary amino color developing agent (as described in, for example, Japanese Patent Application (OPI) No. 135841/81 (the term "OPI" indicates an unexamined published patent application open to public inspection)) and magenta color image forming couplers having a blocking group bonded to the cyclic nitrogen atom of the above-described pyrazolobenzimidazole or imidazolone 1H-pyrazolo [5,1-C][1,2,4]-triazole at a position capable of reacting with the oxidation product of an aromatic primary amino color developing agent (as described in, for example, Japanese Patent Application (OPI) No. 133734/81) have been proposed.

For improving the properties of the latter couplers, various compounds having the same skeletons as the foregoing magenta color image forming couplers and improved blocking groups have been proposed (as described in, for example, Japanese Patent Application (OPI) Nos. 107537/83, 107538/83, 111034/83, 111035/83, 111036/83, 111943/83, 111944/83, 113937/83, 113939/83, 113936/83, 113938/83, 113940/83, 115437/83, etc.). The feasutes of the couplers having these blocking groups are that since one of the dissociative hydrogen atoms of the above-described 4-equivalent magenta couplers or 2-equivalent magenta couplers is blocked by the block group, the magenta color image forming coupler is stabilized to heat, light and oxidation and the coupling rate can be controlled in a manner different from the 2-equivalent couplers. Now, since the above-described couplers have a blocking coupler which can be released by causing a reaction with the oxidation product of an aromatic primary amino color developing agent, silver halide is excessively consumed by 2-equivalent couplers in other stages than the color image forming stage and hence attempts to use such a coupler are not a desirable direction from the viewpoint of saving resources. However, in the case of applying these couplers to everprogressing silver halide color photographic materials for photographing, it becomes an advantage for improving the graininess of the color photographic materials for photographing that silver halide is excessively consumed by 2-equivalent couplers for other purposes than the formation of color images. That is, the foregoing coupler has the advantage that the excessive oxidation product of a developing agent formed at developing exposed photographic materials for photographing usually forms a large amount of dyes to reduce the graininess of images formed but in the case of using the couplers, the silver halide captures the excessive oxidation product of the developing agent, whereby the graininess is improved.

In spite of these excellent principles, the conventional magenta color image forming couplers having a blocking group still have deficiencies in that they are unstable for practical use, they show low colored dye images, and the colored dye images formed by using these couplers are poor in fastness.

SUMMARY OF THE INVENTION

As the result of various investigations for overcoming these difficulties, the inventors have discovered that these difficulties cannot be overcome by using a conventional magenta dye skeleton itself but these difficulties can be overcome by using a new type of coupler of a new skeleton having introduced thereto a block group or of a previously proposed skeleton having a blocking coupler at a different bonding position.

The new skeleton has not yet been publically known and is practically described in Japanese Patent Application (OPI) Nos. 162548/84 and 171956/84.

An object of this invention is, therefore, to provide novel magenta dye forming couplers having an excellent coloring property and a graininess improving effect and also to provide a magenta color image forming process using these couplers.

Another object of this invention is to provide a novel magenta color image forming process using a magenta image forming coupler having excellent stability during storage (excellent shelf life and formalin resistance).

A further object of this invention is to provide a magenta color image forming process using novel magenta color image forming couplers forming dyes having good fastness.

As the result of various investigations, it has been discovered that the above-described objects can be attained by the present invention. The invention is a color image forming process which comprises developing a silver halide color photographic material using an aromatic primary amino developing agent in the presence of a novel blocked magenta dye forming coupler represented by the following general formula (I):

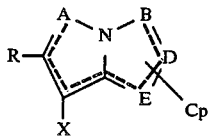 (I)

wherein R represents a hydrogen atom or a substituent; X represents a hydrogen atom, a halogen atom, a carboxy group, or a coupling releasable group; Cp represents a coupling block group capable of forming a colorless or alkali-soluble product by reaction with the oxidation product of a color developing agent; A represents

when Cp is bonded and —N= when Cp is not bonded; B and E each represents

when Cp is bonded and —N= or

when Cp is not bonded; D represents —N= or

(wherein R has the same significance as defined above and said Rs in said B, E and D may be the same or different); and ≡≡≡ represents three movable double bonds; however, said Cp is not bonded to E when A, D and E simultaneously contain a nitrogen atom and B contains a carbon atom. Also, the coupler may form a dimer or more oligomers at R or X, and substituent Rs on adjacent carbon atoms may form a ring with each other.

DETAILED DESCRIPTION OF THE INVENTION

Now, the compound of general formula (I) is explained in detail. The compound of general formula (I) can be, more specifically, shown by general formula (II), (III) or (IV):

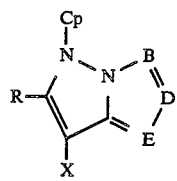 (II)

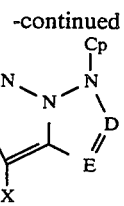 (III)

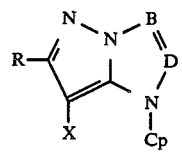 (IV)

wherein R, X, B, D, E and Cp in general formulae (II), (III) and (IV) have the same significance as explained in regard to general formula (I). However, in general formula (IV), the case wherein D is —N= when B is

is excluded.

The compounds shown by general formulae (II), (III) and (IV) are explained below in detail.

R represents a hydrogen atom or a substituent and preferred examples of the substituent are a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imido group, a sulfamoylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, and an aryloxycarbonyl group.

X represents a hydrogen atom, a halogen atom, a carboxy group or a group which is bonded to a carbon atom at the coupling position through an oxygen atom, a nitrogen atom or a sulfur atom and is released at coupling. The coupler may form a dimer or more oligomers at said R or X and Rs on adjacent carbon atoms may form a ring with each other. Also, the coupler shown by general formula (I) may be in the form of a polymer coupler so that the coupler of general formula (I) exists at the side chain of a polymer as a coupler group, and a polymer induced from a vinyl monomer having the moiety shown by general formula (I) is preferred. In this case, at least one of R and X represents a vinyl-containing group.

More specifically, R represents a hydrogen atom, a halogen atom (e.g., a chlorine atom, a bromine atom, etc.), a substituted or unsubstituted alkyl group (e.g., a methyl group, a propyl group, a t-butyl group, a trifluoromethyl group, a tridecyl group, a 3-(2,4-di-t-amylphenoxy)propyl group, an allyl group, a 2-dodecyloxyethyl group, a 3-phenoxypropyl group, a 2-hexylsulfonylethyl group, a cyclopentyl group, a benzyl group, etc.), a substituted or unsubstituted aryl group (e.g., a phenyl group, a 4-t-butylphenyl group, a 2,4-di-t-amylphenyl group, a 4-tetradecanamidophenyl group, etc.), a heterocyclic group (5- to 7-membered cyclic groups including 0, N, S, etc., e.g., a 2-furyl group, a 2-thienyl group, a 2-pyrimidinyl group, a 2-benzothiazolyl group, etc.), a cyano group, an alkoxy group (e.g., a methoxy group, an ethoxy group, a 2-methoxyethoxy group, a 2-dodecyloxyethoxy group, a 2-methanesulfonylethoxy group, etc.), an aryloxy group (e.g., a phenoxy group, a 2-methylphenoxy group, a 4-t-butylphenoxy group, etc.), a heterocyclic oxy group (e.g., a 2-benzimidazolyloxy group, etc.), an acyloxy group (e.g., an acetoxy group, a hexadecanoyloxy group, etc.), a carbamoyloxy group (e.g., an N-phenylcarbamoyloxy group, an N-ethylcarbamoyloxy group, etc.), a silyloxy group (e.g., a trimethylsilyloxy group, etc.), a sulfonyloxy group (e.g., a dodecylsulfonyloxy group, etc.), an acylamino group (e.g., an acetamido group, a benzamido group, a tetradecanamido group, an α-(2,4-di-t-amylphenoxy)butyramido group, a γ-(3-t-butyl-4-hydroxyphenoxy)butyramido group, an α-[4-(4-hydroxyphenylsulfonyl)phenoxy]decanamido group, etc.), an anilino group (e.g., a phenylamino group, a 2-chloroanilino group, a 2-chloro-5-tetradecanamidoanilino group, a 2-chloro-5-tetradecanamidoanilino group, a 2-chloro-5-dodecyloxycarbonylanilino group, an N-acetylanilino group, a 2-chloro-5-[α-(3-t-butyl-4-hydroxyphenoxy)-dodecanamido]anilino group, etc.), a ureido group (e.g., a phenylureido group, a methylureido group, an N,N-dibutylureido group, etc.), an imido group (e.g., an N-succinimido group, a 3-benzylhydantoinyl group, a 4-(2-ethylhexanoylamino)phthalimido group etc.), a sulfamoylamino group (e.g., an N,N-dipropylsulfamoylamino group, an N-methyl-N-decylsulfamoylamino group, etc.), a carbamoylamino group (e.g., a p-cyanophenylcarbamoylamino group, a p-chlorophenylcarbamoylamino group, etc.), an alkylthio group (e.g., a methylthio group, an octylthio group, a tetradecylthio group, a 2-phenoxyethylthio group, a 3-phenoxypropylthio group, a 3-(4-t-butylphenoxy)propylthio group, etc.), an arylthio group (e.g., a phenylthio group, a 2-butoxy-5-t-octylphenylthio group, a t-octylphenylthio group, a 3-pentadecylphenylthio group, a 2-carboxyphenylthio group, a 4-tetradecanamidophenylthio group, etc.), a heterocyclic thio group (e.g., a 2-benzothiazolylthio group, etc.), an alkoxycarbonylamino group (e.g., a methoxycarbonylamino group, a tetradecyloxycarbonylamino group, etc.), an aryloxycarbonylamino group (e.g., a phenoxycarbonylamino group, a 2,4-di-tert-butylphenoxycarbonylamino group, etc.), a sulfonamido group (e.g., a methanesulfonamido group, a hexanedecanesulfonamido group, a benzenesulfonamido group, a p-toluenesulfonamido group, an octadecanesulfonamido group, a 2-methyloxy-5-t-butylbenzenesulfonamido group, etc.), a carbamoyl group (e.g., an N-ethylcarbamoyl group, an N,N-dibutylcarbamoyl group, an N-(2-dodecyloxyethyl)carbamoyl group, an N-[3-(2,4 -di-tert-amylphenoxy)propyl]carbamoyl group, etc.), an acyl group (e.g., an acetyl group, a (2,4-di-tert-amylphenoxy)acetyl group, a benzoyl group, etc.), a sulfamoyl group (e.g., an N-ethylsulfamoyl group, an N,N-dipropylsulfamoyl group, an N-(2-dodecyloxyethyl)sulfamoyl group, an n-ethyl-N-dodecylsulfamoyl group, an N,N-diethylsulfamoyl group, etc.), a sulfonyl group (e.g., a methanesulfonyl group, an octanesulfonyl group, a benzenesulfonyl group, a toluenesulfonyl group, etc.), a sulfinyl group (e.g., an octanesulfinyl group, a dodecanesulfinyl group, a benzenesulfinyl group, etc.), an alkoxycarbonyl group (e.g., a methoxycarbonyl group, a butoxycarbonyl group, a dodecylcarbonyl group, an octadecylcarbonyl group, etc.), or an aryloxycarbonyl group (e.g., a phenyloxycarbonyl group, a 3-pentadecyloxycarbonyl group, etc.).

Also, X represents a hydrogen atom, a halogen atom (e.g., a chlorine atom, a bromine atom, an iodine atom, etc.), a carboxy group, a group bonded through an oxygen atom (e.g., an acetoxy group, a propanoyloxy group, a benzoyloxy group, a 2,4-dichlorobenzoyloxy group, an ethoxyoxaloyloxy group, a pyruvinyloxy group, a cinnamoyloxy group, a phenoxy group, a 4-cyanophenoxy group, a 4-methanesulfonamidophenoxy group, a 4-methanesulfonylphenoxy group, an α-naphthoxy group, a 3-penta-decylphenoxy group, a benzyloxycarbonyloxy group, an ethoxy group, a 2-cyanoethoxy group, a benzyloxy group, a 2-phenethyloxy group, a 2-phenoxyethoxy group, a 5-phenyltetrazolyloxy group, a 2-benzothiazolyloxy group, etc.), a group bonded through a nitrogen atom (e.g., a benzenesulfonamido group, an N-ethyltoluenesulfonamido group, a heptafluorobutanamido group, a 2,3,4,5,6-pentafluorobenzamido group, an octanesulfonamido group, a p-cyanophenylureido group, an N,N-diethylsulfamoylamino group, a 1-piperidyl group, a 5,5-dimethyl-2,4-dioxo-oxazolidinyl group, a 1-benzylethoxy-3-hydantoinyl group, a 2N-1,1-dioxo-3(2H)-oxo-1,2-benzointhiazolyl group, a 2-oxo-1,2-dihydro-1-pyridinyl group, an imidazolyl group, a pyrazolyl group, a 4-acetamido-1-pyrazolyl group, a 3,5-dimethylpyrazolyl group, a 4-(3-hydroxypropyl)-1-pyrazolyl group, a 3,5-diethyl-1,2,4-triazole-1-yl group, a 5- or 6-bromobenzotriazole-1-yl group, a 5-methyl-1,2,3,4-triazole-1-yl group, a benzimidazolyl group, a 3-benzyl-1-hydantoinyl group, a 1-benzyl-5-hexadecyloxy-3-hydantoinyl group, a 5-methyl-1-tetrazolyl group, etc., an arylazo group (e.g., a 4-methoxyphenylazo group, a 4-pivaloylamino-3-hydroxyphenylazo group, a β-naphthylazo group, a 4-hydroxy-3-methylphenylazo group, a 4-pivaloylaminophenylazo group, etc.)), or a group bonded through a sulfur atom (e.g., a phenylthio group, a 2-carboxyphenylthio group, a 2-methoxy-5-t-octylphenylthio group, a 4-methanesulfonylphenylthio group, a 4-octanesulfonamidophenylthio group, a 2-butoxyphenylthio group, a 2-(2-hexanesulfonylethyl)-5-tert-octylphenylthio group, a benzylthio group, a 2-cyanoethylthio group, a 1-ethoxycarbonyltridecylthio group, a 5-phenyl-2,3,4,5-tetrazolylthio group, a 2-benzothiazolylthio group, a 2-dodecylthio-5-thiophenylthio group, a 2-phenyl-3-dodecyl-1,2,4-triazolyl-5-thio group, etc.).

Now, a divalent group of R or X forming a bis compound is explained in more detail.

That is, R represents a substituted or unsubstituted alkylene group (e.g., a methylene group, an ethylene group, a 1,10-decylene group, —CH$_2$CH$_2$—O—CH$_2$CH$_2$—, etc.), a substituted or unsubstituted phenylene group (e.g., a 1,4-phenylene group, a 1,3-phenylene group,

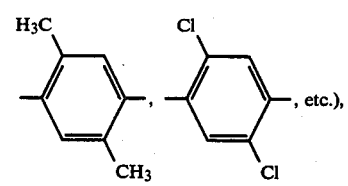

—NHCO—R$_5$—CONH—(wherein R$_5$ represents a substituted or unsubstituted alkylene or phenylene group; examples of the above group are —NHCOCH$_2$CH$_2$CONH—,

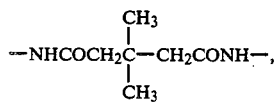

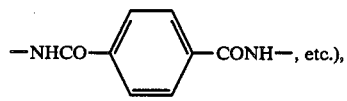

or —S—R$_6$—S— (wherein R$_6$ represents a substituted or unsubstituted alkylene group; examples of the above group are —S—CH$_2$CH$_2$—S—,

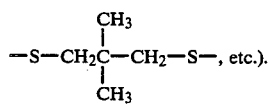

Also, X is a divalent group formed from the above-described monovalent group selected from a group bonded through an oxygen atom, a group bonded through a nitrogen atom, and a group bonded through a sulfur atom.

When the coupler shown by general formula (I) is present in a vinyl monomer, the vinyl group may have a substituent in addition to the coupler shown by general formula (I) and specific examples of the substituent are a hydrogen atom, a chlorine atom, or a lower alkyl group having 1 to 4 carbon atoms (e.g., a methyl group, an ethyl group, etc.).

The monomer containing the coupler shown by general formula (I) may form a monomer with a non-coloring ethylenic monomer which does not cause coupling with the oxidation product of an aromatic primary amino developing agent.

Examples of the non-coloring ethylenic monomer which does not cause coupling with the oxidation product of an aromatic primary amino developing agent are acrylic acid, α-chloroacrylic acid, α-alkylacrylic acid and the esters or amides induced from these acrylic acids (e.g., acrylamide, n-butylacrylamide, t-butylacrylamide, diacetonacrylamide, methacrylamide, methyl acrylate, ethyl acrylate, n-propyl acrylate, n-butyl acrylate, t-butyl acrylate, isobutyl acrylate, 2-ethylhexyl acrylate, n-octyl acrylate, lauryl acrylate, methyl methacrylate, ethyl methacrylate, n-butyl methacrylate, α-hydroxy methacrylate, etc.), methylenebisacrylamide, vinyl esters (e.g., vinyl acetate, vinyl propionate, vinyl laurate, etc.), acrylonitrile, methacrylonitrile, aromatic vinyl compounds (e.g., styrene and derivatives thereof, vinyltoluene, divinylbenzene, vinylacetophenone, sulfostyrene, etc.), itaconic acid, citraconic acid, crotonic acid, vinylidene chloride, vinyl alcohol ethers (e.g., vinyl ethyl ether, etc.), maleic acid, maleic anhydride, maleic acid esters, N-vinyl-2-pyrrolidone, N-vinylpyridine, 2- or 4-vinylpyridine, etc.

The aforesaid non-coloring ethylenically unsaturated monomers can be used solely or as a mixture. Examples of the combination are n-butyl acrylate and methyl acrylate, styrene and methacrylic acid, methacrylic acid and acrylamide, methyl acrylate and diacetonacrylamide, etc.

The non-coloring ethylenically unsaturated monomer for forming a copolymer with the solid water-insoluble monomer coupler is selected, as well known in the field of polymer couplers, in such a manner that the copolymer having the most suitable physical properties and/or chemical properties such as solubility, compatibility with a binder for photographic colloid compositions, e.g., gelatin, etc., flexibility, heat stability, etc., is formed.

The polymer coupler for use in this invention may be water-soluble or water-insoluble and, in particular, a polymer coupler latex is preferred.

In the above formulae, Cp represents a coupling block group which forms a colorless or alkali-soluble reaction product after the reaction with an oxidized color developing agent and is bonded to the coupler at the coupling position and is, preferably, shown by the following general formula (V), (VI), (VII), (VIII) or (IX):

wherein R$_2$ represents an alkoxycarbonyl group, an aryloxycarbonyl group, a heterocyclic oxycarbonyl group, an alkylcarbamoyl group, an arylcarbamoyl group, a heterocyclic carbamoyl group, an alkylcarbonyl group, an arylcarbonyl group, a heterocyclic carbonyl group, an alkoxythiocarbonyl group, an aryloxythiocarbonyl group, an alkylsulfonyl group, an arylsulfonyl group, a heterocyclic sulfonyl group, an alkylsulfinyl group, an arylsulfinyl group, a heterocyclic sulfinyl group, an alkylsulfamoyl group, an arylsulfamoyl group, a heterocyclic sulfamoyl group, a nitro group, a cyano group, or a carboxy group, and R$_3$ represents, in addition to the group as defined for R$_2$, a hydrogen atom, a halogen atom, an alkyl group (straight chain, branched, or cyclic), an aryl group, an alkoxy group, an aryloxy group, an alkylthio group, an arylthio group, an acyloxy group, an amino group, an alkylcarbamoyl group, an arylcarbamoyl group, an acylcarbamoyl group, or a heterocyclic ring. Also, said R$_2$ and R$_3$ may cyclize with each other to form a 5- or 6-membered hydrocarbon ring or a 5- or 6-membered heterocyclic ring having a carbonyl group at the α-position to

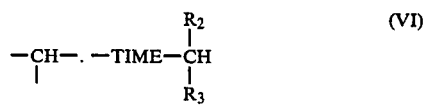

wherein R$_2$ and R$_3$ have the same significance as stated for the foregoing general formula (V) and TIME represents a group that causes an intramolecular nucleophilic reaction after releasing the group -TIME by the reaction of and the oxidation product of a color developing agent or a group that causes electron migration along a covalent system.

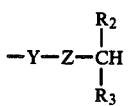  (VII)

wherein $R_2$ and $R_3$ have the same significance as defined for general formula (V); Y represents an oxygen atom or a sulfur atom and Z represents a carbonyl group, a thiocarbonyl group, an oxalyl group, a sulfonyl group, a sulfinyl group, a methylene group or a substituted methylene group.

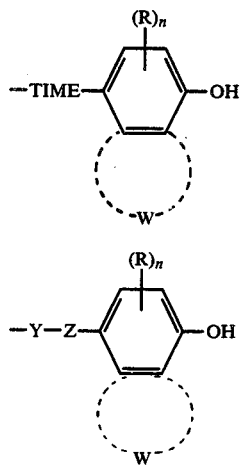

In general formulae (VIII) and (IX),

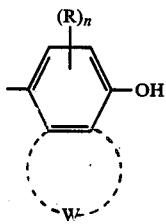

represents a cyan dye forming coupler residue having a phenol nucleus or naphthol nucleus; W represents an atomic group forming a naphthol nucleus by causing condensation with a phenyl nucleus; R has the same significance as defined above; n represents an integer of 1 to 4 when the foregoing cyan dye forming coupler has a phenol nucleus or an integer of 1 to 6 when the coupler has a naphthol nucleus; and TIME has the same significance as defined for general formula (VI) and —Y—Z— has the same significance as defined for general formula (VII). In this case, when n is 2 or more, Rs may be the same or different.

Now, the substituents shown in the above general formulae (V), (VI), (VII), (VIII) or (IX) are explained in more detail.

$R_2$ represents an alkoxycarbonyl group (e.g., a methoxycarbonyl group, a dodecyloxycarbonyl group, a benzyloxycarbonyl group, a cyclohexyloxycarbonyl group, etc.), an aryloxycarbonyl group (e.g., a phenoxycarbonyl group, etc.), a heterocyclic oxycarbonyl group (e.g., a 3-pyridyloxycarbonyl group, a 2-tetrahydropyranyloxycarbonyl group, a 2-thienyloxycarbonyl group, etc.), an alkylcarbamoyl group (e.g., an N-methylcarbamoyl group, an N-methyl-N-(4-carboxyphenyl)carbamoyl group, an N,N-diethylcarbamoyl group, an N-cyclohexylcarbamoyl group, etc.), an arylcarbamoyl group (e.g., an N-phenylcarbamoyl group, an N-(4-carboxyphenyl)carbamoyl group, an N-(3,5-dicarboxyphenyl)carbamoyl group, an N-(2-chloro-5acetamidophenyl)carbamoyl group, a 2-N-naphthylcarbamoyl group, an N-(4-ethoxycarbonylphenyl)carbamoyl group, etc.), a heterocyclic carbamoyl group (e.g., an N-(2-pyridyl)carbamoyl group, an N-ethyl-N-(4-pyrimidinyl)carbamoyl group, etc.), an alkylcarbonyl group (e.g., an acetyl group, a pivaloyl group, an i-butyroyl group, a cyclohexanoyl group, a 3-bitynoyl group, a cyclopropanecarbonyl group, a phenylacetyl group, etc.), an arylcarbonyl group (e.g., a benzoyl group, a 4-methoxy-benzyl group a 3-chlorobenzoyl group, a β-naphthoyl group, a 4-tert-butylbenzoyl group, etc.), a heterocyclic carbonyl group (e.g., a 2-pyridinecarbonyl group, etc.), an alkoxythiocarbonyl group (e.g., a benzyloxythiocarbonyl group, an ethoxythiocarbonyl group, etc.), an arylthiocarbonyl group (e.g., a phenoxythiocarbonyl group, etc.), an alkylsulfonyl group (e.g., a methane-sulfonyl group, an octanesulfonyl group, a dodecane-sulfonyl group, a 2-ethylhexanesulfonyl group, etc.), an arylsulfonyl group (e.g., a benzenesulfonyl group, a p-toluenesulfonyl group, a p-acetamidophenylsulfonyl group, etc.), a heterocyclic sulfonyl group (e.g., a 2-pyridinesulfonyl group, a 2-thiophenesulfonyl group, etc.), an alkylsulfinyl group (e.g., a methanesulfinyl group, an octanesulfinyl group, etc.), an arylsulfinyl group (e.g., a benzenesulfinyl group, etc.), a heterocyclic sulfinyl group (e.g., a 4-pyridinesulfinyl group, a 5-quinolinesulfinyl group, etc.), an alkylsulfamoyl group (e.g., an N-ethylsulfamoyl group, an N-benzylsulfamoyl group, etc.), an arylsulfamoyl group (e.g., an N-phenylsulfamoyl group, an N-ethyl-N-phenylsulfamoyl group, an N-(4-methoxycarbonylphenyl)sulfamoyl group, an N-(2-chlorophenyl)sulfamoyl group, etc.), a heterocyclic sulfamoyl group (e.g., an N-(2-pyridyl)sulfamoyl group, an N-(2-quinolyl)sulfamoyl group, etc.), a nitro group, a cyano group, or a carboxy group.

$R_3$ represents, in addition to the same group as defined for $R_2$, a hydrogen atom, a halogen atom (e.g., a chlorine atom, a bromine atom, etc.), an alkyl group (e.g., a methyl group, a t-butyl group, an i-propyl group, a cyclohexyl group, an allyl group, etc.), an aryl group (e.g., a phenyl group, a 4-nitrophenyl group, a 2-nitro-4-cyanophenyl group, a 4-cyanophenyl group, a 4-methanesulfonylphenyl group, etc.), an alkoxy group (e.g., a methoxy group, an ethoxy group, a benzyloxy group, etc.), an arylxoy group (e.g., a phenoxy group, a 4-nitrophenoxy group, etc.), an alkylthio group (e.g., an ethoxythio group, a benzylthio group, a 2-cyclohexane-1-thio group, etc.), an arylthio group (e.g., a phenylthio group, a 4-chlorophenylthio group, a 4-methoxyphenylthio group, a 4-cyanophenylthio group, a 2-chloro-4-tetradecanamidophenylthio group, a 2-butoxy-t-octylphenylthio group, etc.), an acyloxy group (e.g., an acetoxy group, a benzoyloxy group, a 2-pyridinecarbonyloxy group, a hexanoyloxy group, etc.), an amino group (e.g., an amino group, an anilino group, a 2-chloroanilino group, a cyclopentylamino group, an α-ethoxycarbonyltridecylthio group, an N-piperidino group, an N-morpholino group, etc.), an alkylcarbamoyl group (e.g., an ethylcarbamoyl group, etc.), an arylcarbamoyl group (e.g., a phenylcarbamoyl group, a 4-methoxyphenylcarbamoyl group, a 2-chloro-4-methanesulfonylphenylcarbamoyl group, etc.), an acylcarbamoyl group (e.g., an N-acetylcarbamoyl group, an N-benzoylcarbamoyl group, etc.), or a heterocyclic ring (e.g., a 2-pyridyl group, a 2-pyrimidyl group, a 2-thiophenyl group, a 2-furyl group, etc.). Also, $R_2$ and $R_3$ may cyclize with each other to form a 5- or 6-membered hydrocarbon ring having a carbonyl group at the α-position to

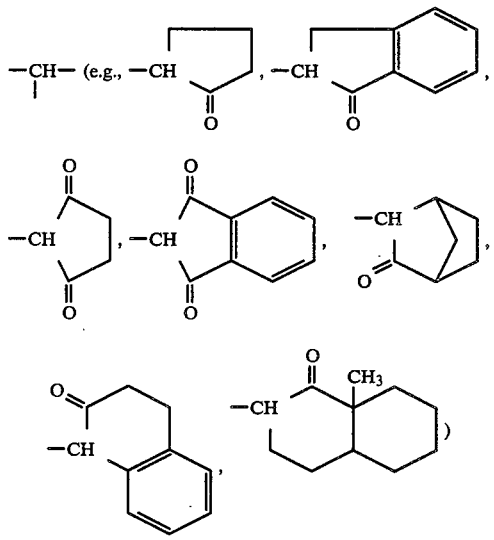

or a 5- or 6-membered heterocyclic ring

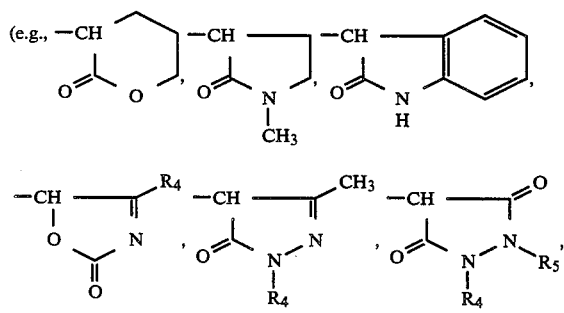

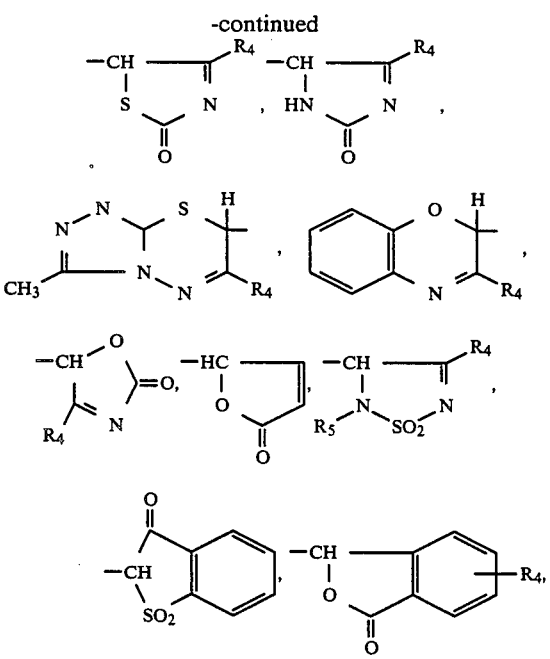

wherein $R_4$ and $R_5$ represent a hydrogen atom or the alkyl group, the aryl group, the alkoxy group, the aryloxy group, the alkylthio group, the arylthio group, the amino group, the acylamino group, the carbamoyl group, the sulfamoyl group, the sulfonamido group, the sulfonyl group, the sulfinyl group, or the acyl group as defined for $R_3$).

TIME shown in general formula (VI) represents a timing control type group disclosed in U.S. Pat. No. 4,248,962, U.S. Pat. No. 4,409,323, Japanese Patent Application (OPI) Nos. 114946/81, 56837/82, 188035/82 and 98728/83, and Research Disclosure, No. 21228 (Dec., 1981).

Y shown in general formula (VII) represents an oxygen atom or a sulfur atom and Z represents a carbonyl group, a thiocarbonyl group, an oxalyl group, a sulfonyl group, a sulfinyl group, a methylene group, or a substituted methylene group (e.g., a methylmethylene group, an ethylmethylene group, a phenylmethylene group, a 2-pyridylmethylene group, a 1-imidazolylmethylene group, etc.).

The blocked magenta color image forming couplers and the vinyl monomers of them for use in this invention are illustrated below but the couplers for use in this invention are not limited to them.

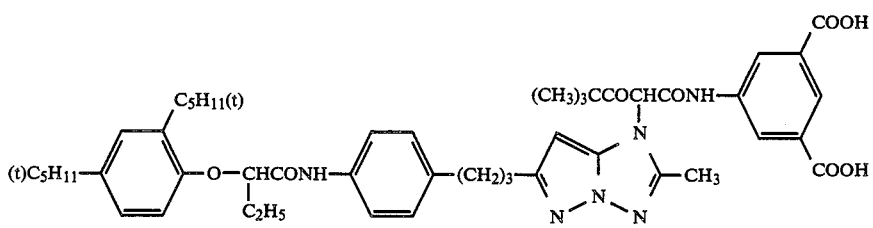

(1)

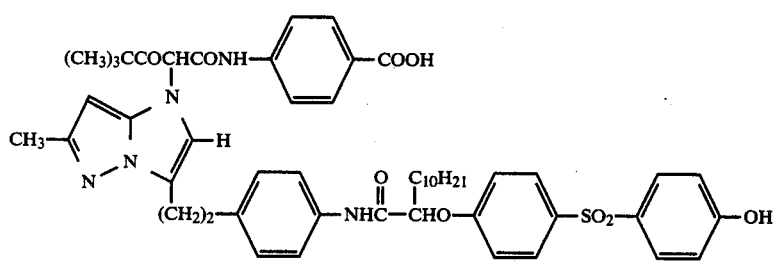
(2)
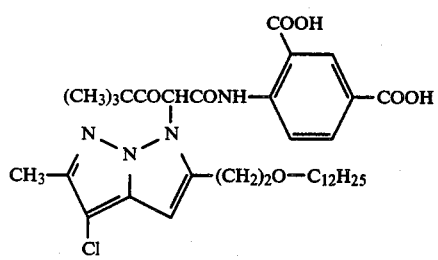
(3)
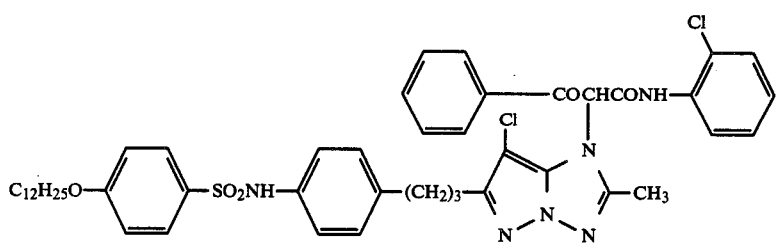
(4)
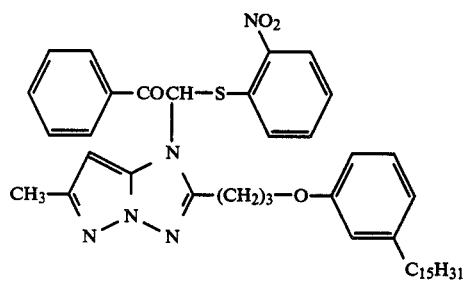
(5)
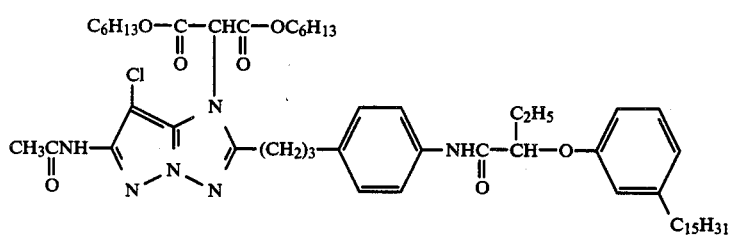
(6)
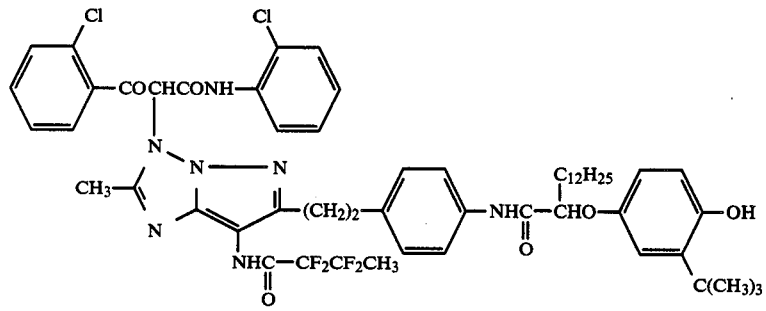
(7)

-continued
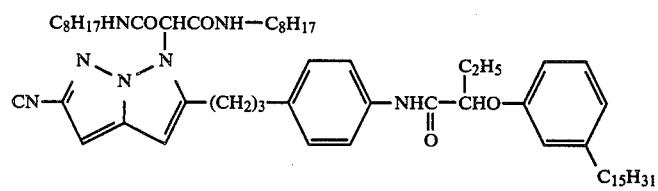 (8)
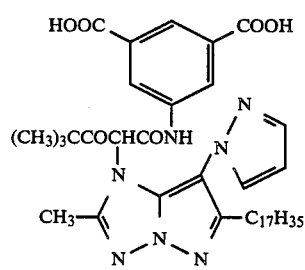 (9)
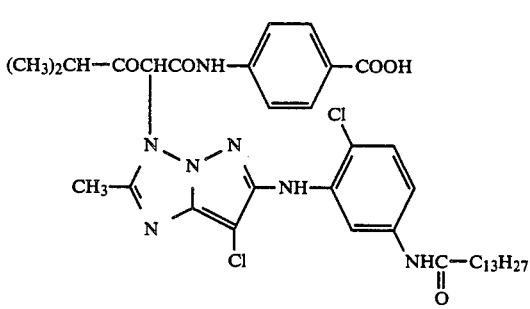 (10)
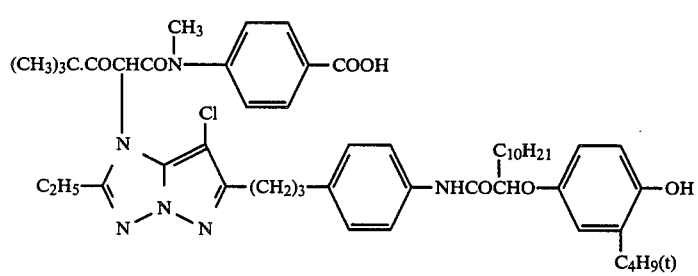 (11)
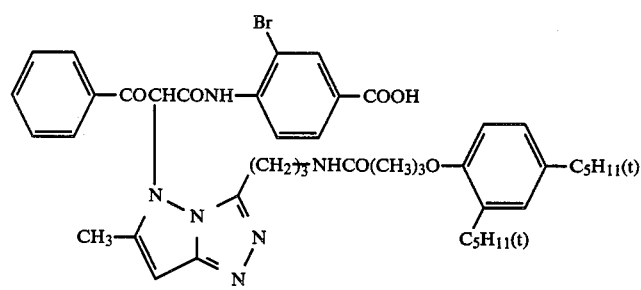 (12)
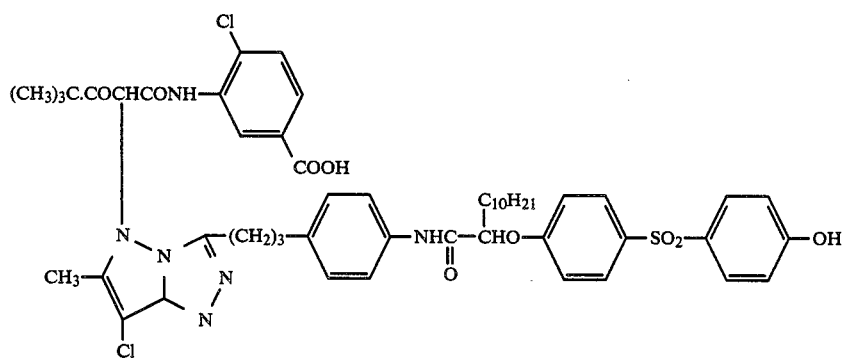 (13)

-continued
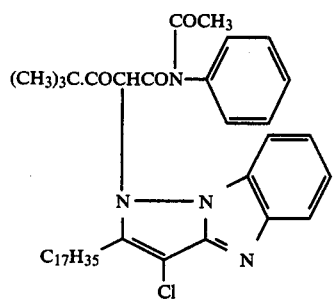
(14)
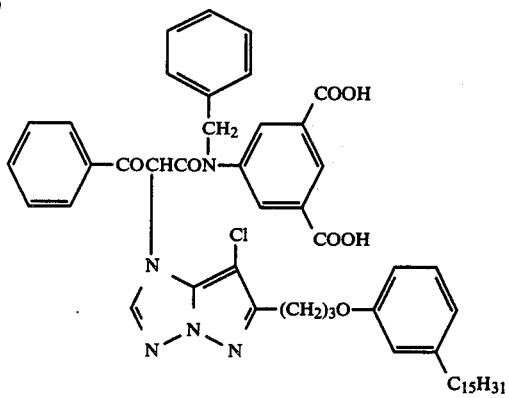
(15)
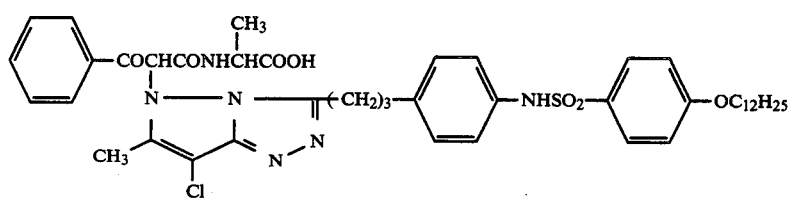
(16)
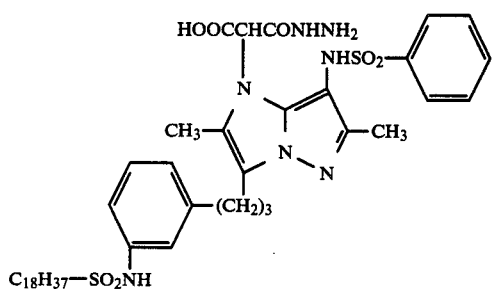
(17)
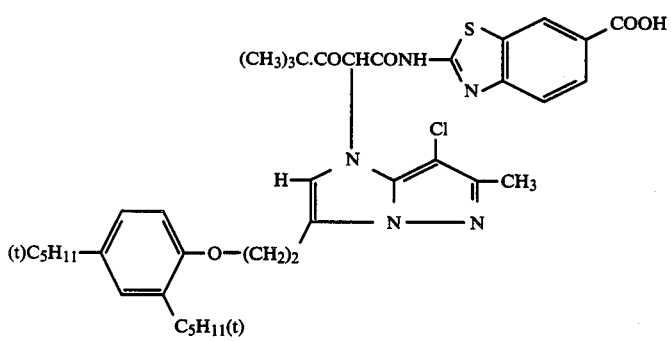
(18)
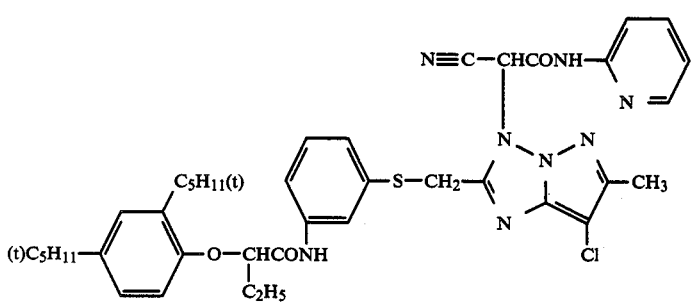
(19)

-continued
(20)
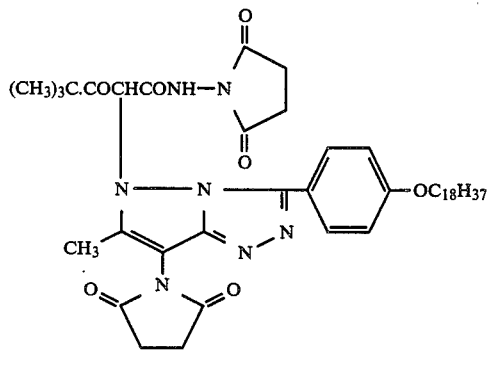
(21)
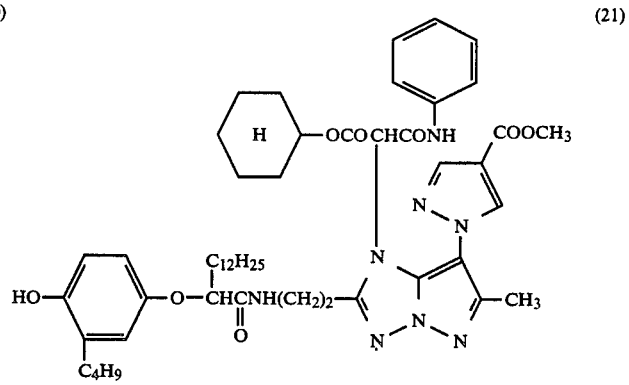
(22)
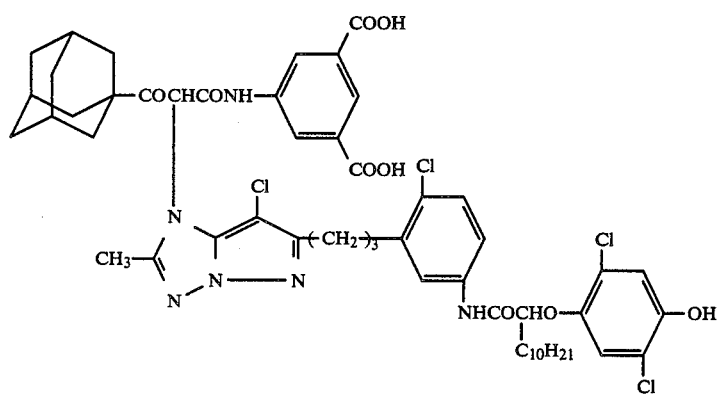
(23)
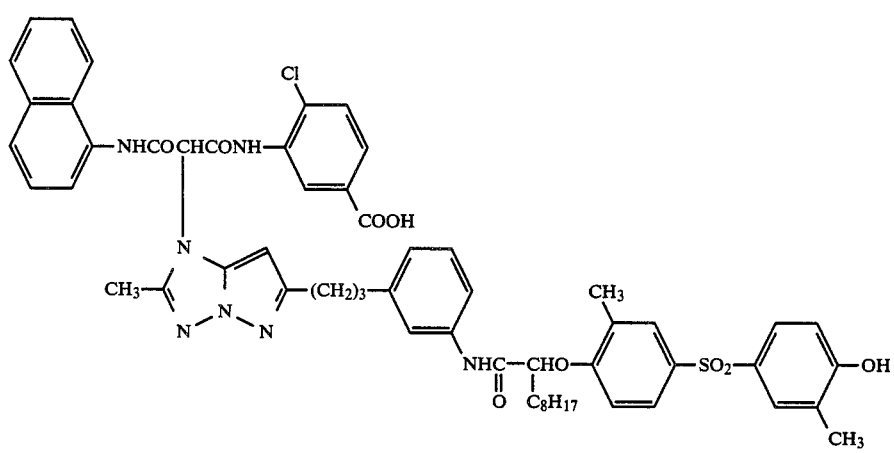
(24)
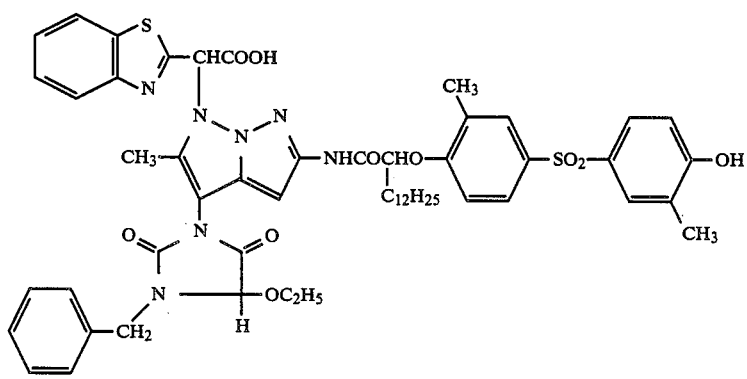

-continued
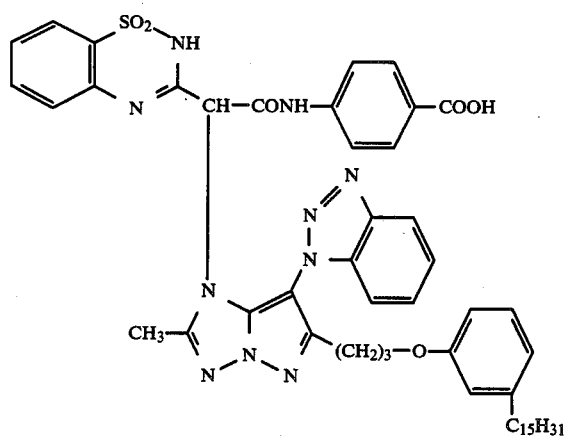
(25)
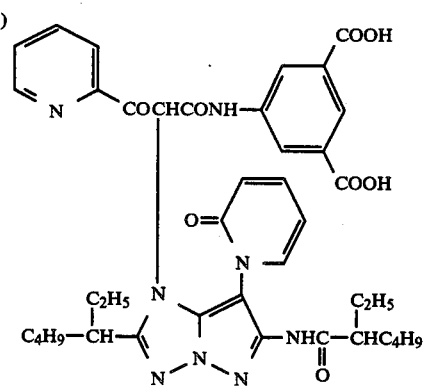
(26)
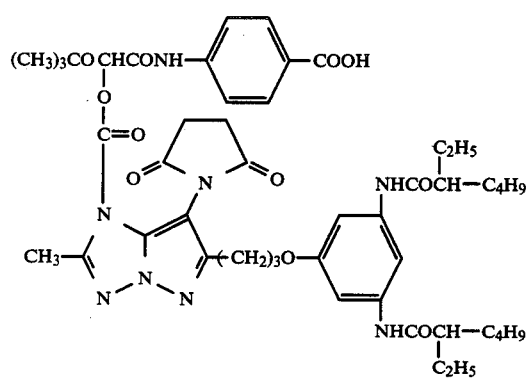
(27)
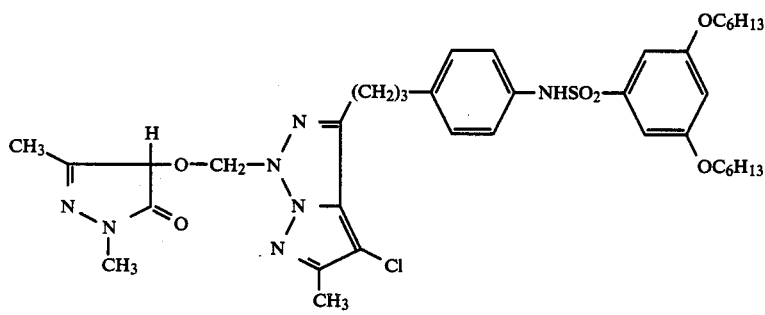
(28)
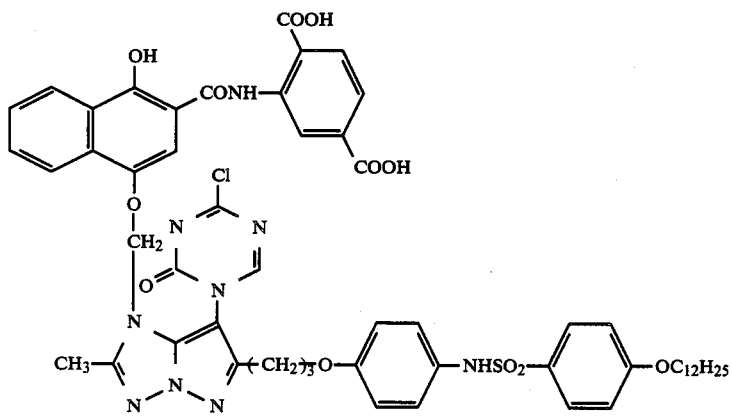
(29)

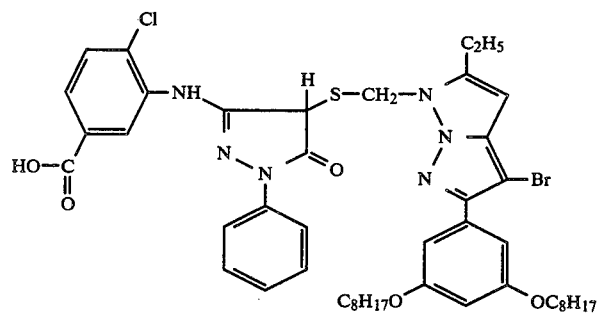
(30)
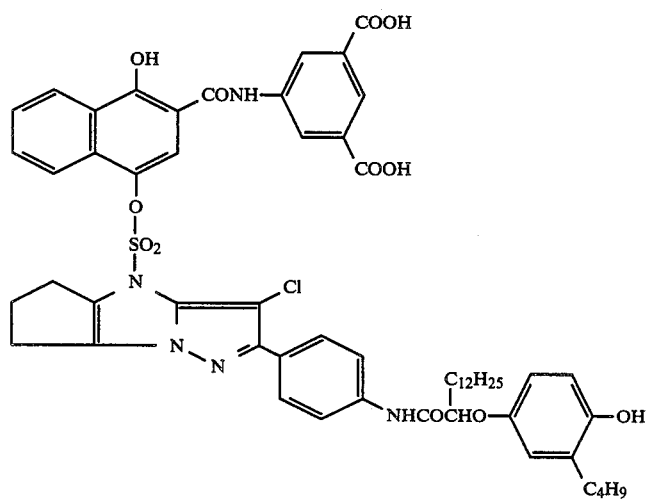
(31)
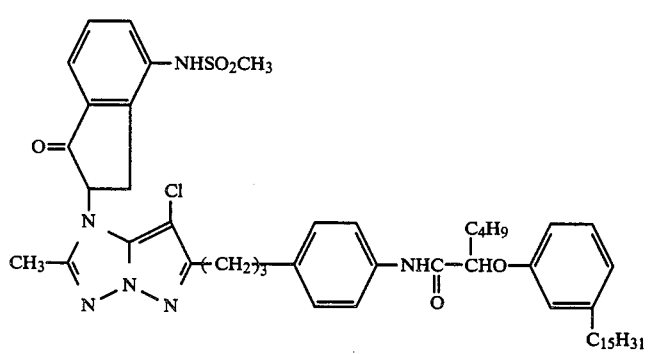
(32)
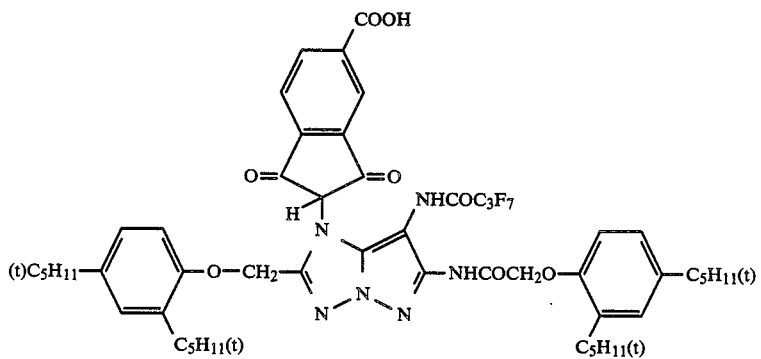
(33)

(34)
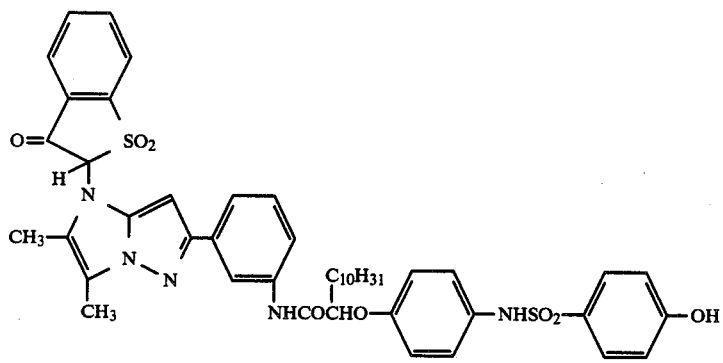
(35)
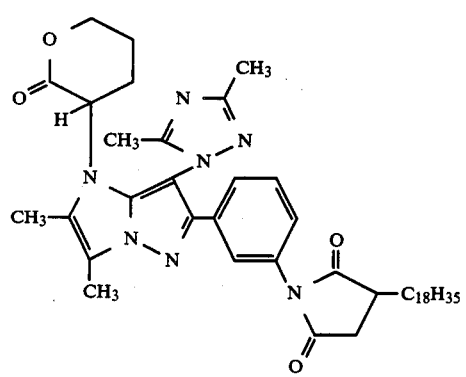
(36)
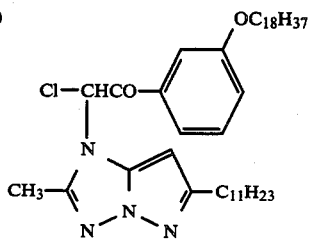
(37)
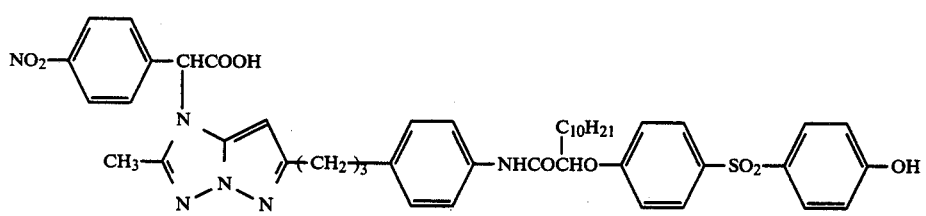
(38)
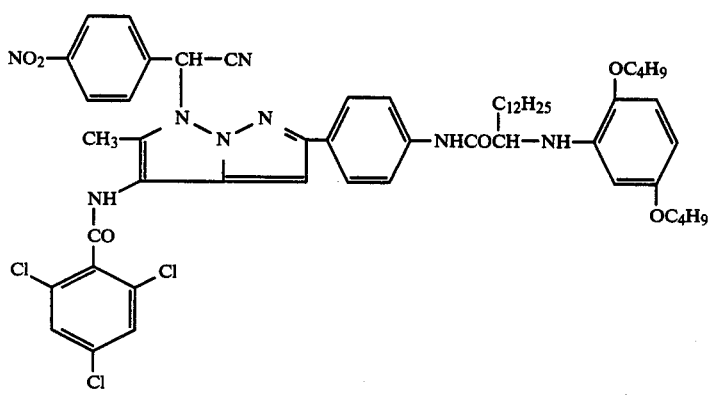

-continued
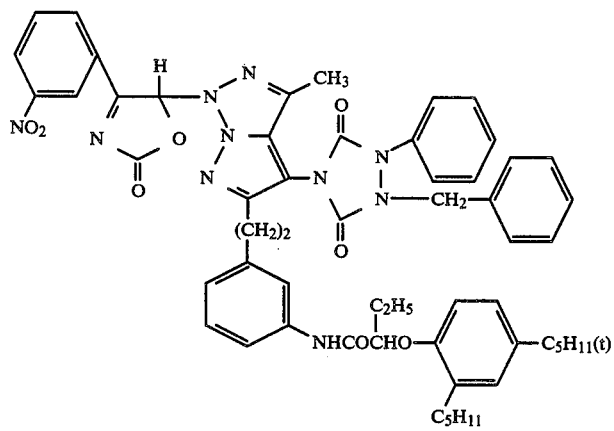
(39)
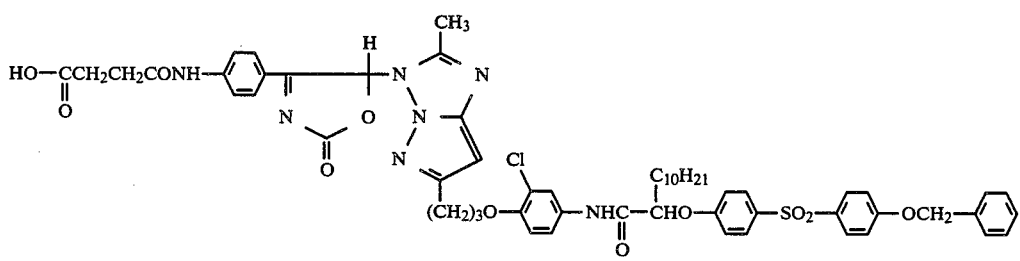
(40)
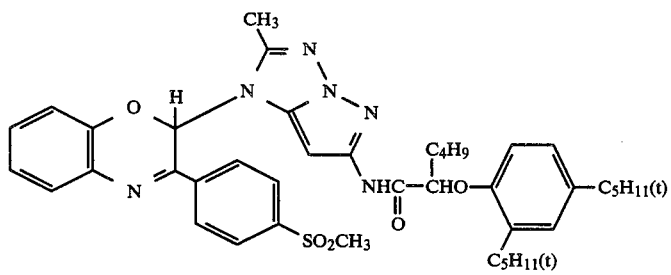
(41)
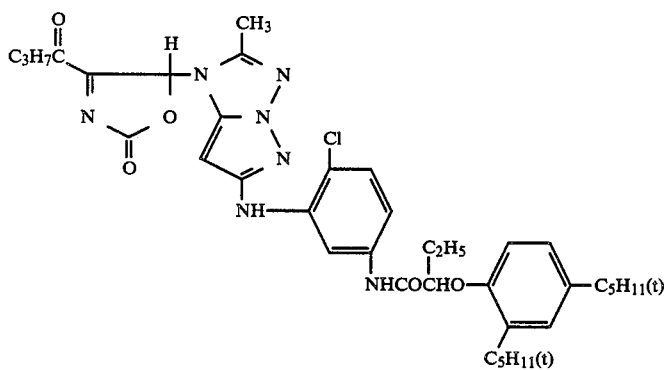
(42)
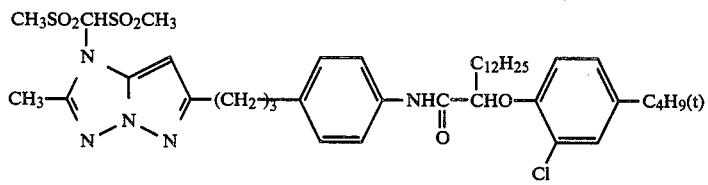
(43)

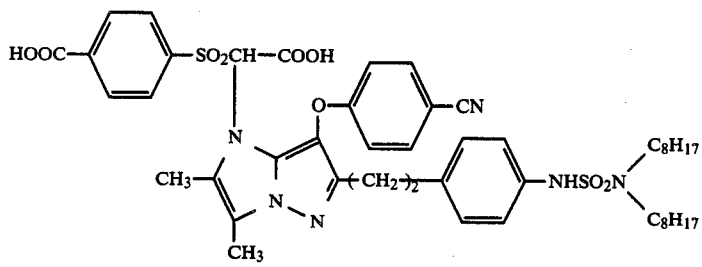

(44)

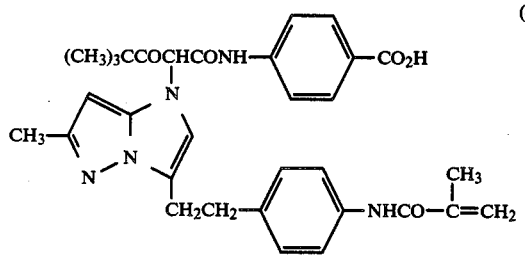

(45)

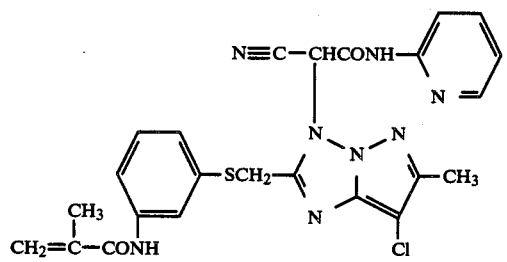

(46)

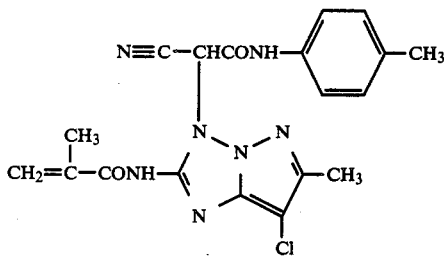

(47)

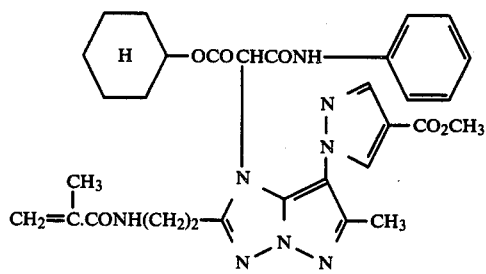

(48)

General synthesis methods for the couplers for use in this invention are described below.

(1) When the block group is directly bonded to the nitrogen atom of the magenta color image forming coupler skeleton in this invention as shown in general formula (V), the coupler can be prepared by the method described in Japanese Patent Application (OPI) No. 133734/81.

That is, the magenta color image forming coupler skeleton is dissociated with a base (e.g., potassium hydroxide, sodium hydroxide, sodium hydride, triethylamine, 1,5-diazabicyclo [5,4,0]undec-5-ene (DBU), etc.) and reacts with a compound having introduced therein a halogen atom (e.g., a chlorine atom, a bromine atom, etc.) to the coupling active position of a block group in a proper solvent (e.g., ethanol, ethyl acetate, chloroform, toluene, dimethylformamide, dimethylacetamide, N-methylpyrrolidone, sulforan, hexamethylphosphotriamide, etc.):

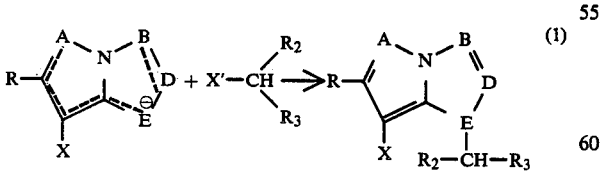

(1)

Also, with the recent progress of organic synthesis chemistry, it becomes possible to make any nitrogen atom of a magenta color image forming coupler skeleton, said nitrogen atom having a mobile proton, react with a block group according to a purpose.

That is, in the above-described ordinary method, the block group is bonded at the position of E as shown in formula (1), but the block group can be bonded to the position of A or B by first introducing a proper protective group (e.g., a benzyl group, a trialkylsilyl group, an acetyl group, etc.) to the position E of the magenta color image forming coupler skeleton and reacting the coupler skeleton with a compound having a halogen atom introduced to the coupling active position of a block group with the absence of a base as shown in the following formula (2).

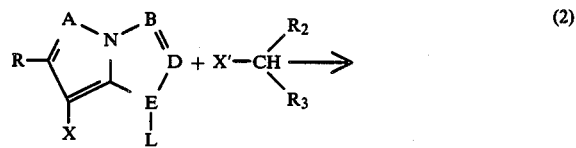

(2)

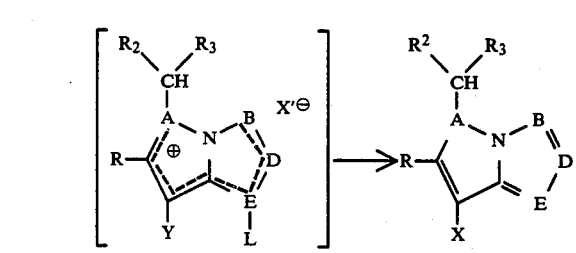

In foregoing reaction formulae (1) and (2), A, B, D, E, R, X, $R_2$ and $R_3$ have the same significance as defined above; X' represents a halogen atom (e.g., a chlorine atom, a bromine atom, etc.), and L represents a protective group (e.g., a benzyl group, a trialkylsilyl group, an acetyl group, etc.).

(2) The compound wherein a timing controlling group such as -TIME- is introduced between the block group and the magenta color image forming coupler skeleton of this invention as shown by general formula (VI) can be prepared by the known method described in, for example, U.S. Pat. 4,248,062, Japanese Patent Application (OPI) Nos. 114946/81, 56837/82, 154234/82, 188635/82 and 98728/83.

(3) The compound shown by general formula (VII) can be prepared by the method described in Japanese Patent Application (OPI) Nos. 113939/83 and 113938/83.

(4) The compound shown by general formula (VIII) or (IX) can be prepared by the method described in Japanese Patent Application (OPI) Nos. 11393/83, 113938/83 and 90932/82 as in the case of (3).

Practical examples of the syntheses of the couplers for use in this invention are shown below.

and the resultant mixture was further stirred for 2 hours. To the reaction mixture thus obtained was added 500 ml of ethyl acetate and the organic layer thus formed was collected and washed with an aqueous saturated sodium chloride solution. After drying the ethyl acetate layer with anhydrous sodium sulfate, the solvent was removed and the residue was treated by silica gel column chromatography (chloroform:ethanol=20:1, the desired compound was a compound having the lowest polarity and a large Rf value). Thus, 42.5 g of desired Compound C was obtained as a powder having no clear melting point.

(b) Synthesis of Coupler (1):

After dissolving 40 g of Compound C in 300 ml of a methanol solution of 10% KOH, the solution was stirred for 1 hour at room temperature. After confirming by thin layer chromatography that the compound was completely hydrolyzed, acetic acid was gradually added dropwise to the solution to neutralize the reaction mixture. After concentrating the reaction mixture

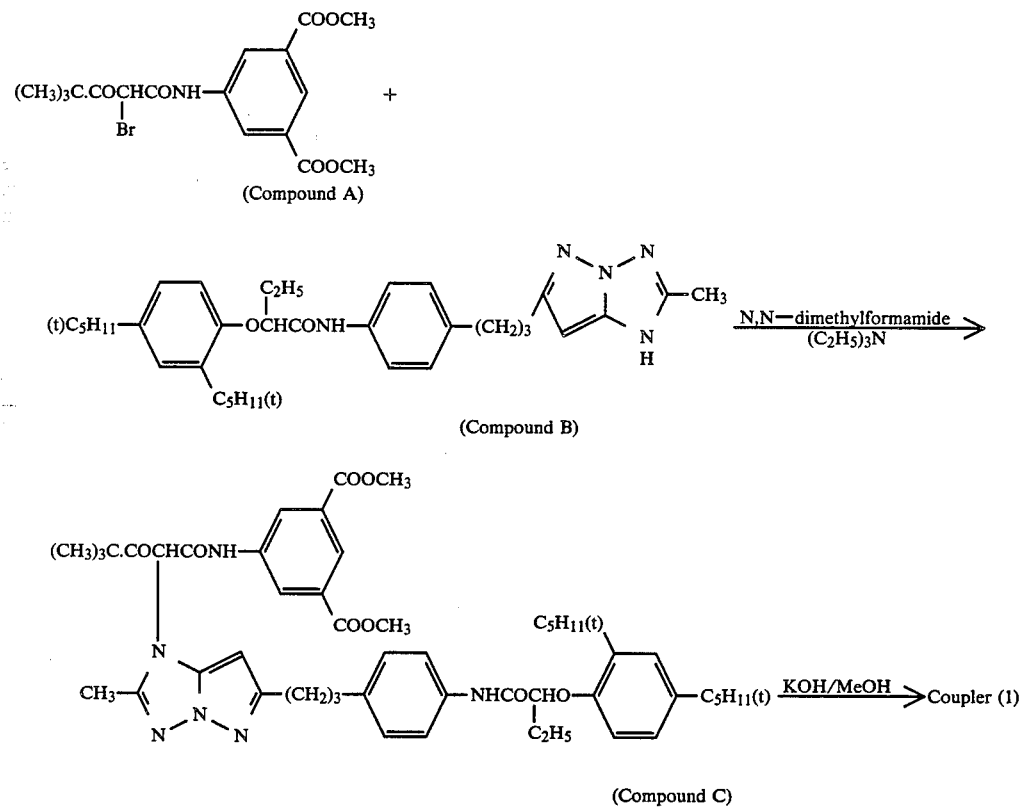

(Compound A)

(Compound B)

(Compound C)

(a) Synthesis of Compound C:

In 300 ml of dimethylformamide were dissolved 41.4 g of Compound A (the compound can be easily obtained by brominating a yellow 4-equivalent mother nucleus by an ordinary method) and 55.8 g of Compound B (prepared by the method described in Japanese Patent Application (OPI) No. 171956/84) and while stirring the solution at room temperature, 15 g of triethylamine was added dropwise to the solution. Then, after stirring the mixture for 2 hours, 20 g of Compound A and 10 g of triethylamine were further added thereto to ½ of the original volume, 500 g of iec-water was added and the precipitates thus deposited were collected and dried to provide 37.6 g of colorless Coupler (1) in an almost pure state.

| Elemental Analysis for $C_{49}H_{62}N_6O_8$: | | | |
|---|---|---|---|
| | C | H | N |
| Calculated (%): | 68.19 | 7.24 | 9.74 |
| Found (%): | 69.20 | 7.21 | 9.70 |

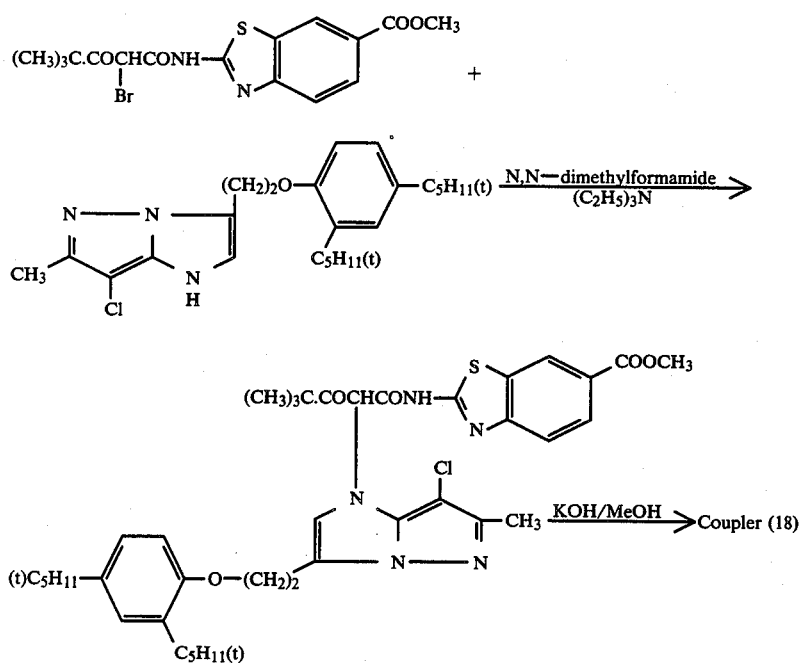

(Compound D)

(Compound E)

(Compound F)

(a) Synthesis of Compound F:

In 500 ml of dimethylformamide were dissolved 41.3 g of Compound D and 41.6 g of Compound E (prepared by the method described in Japanese Patent Application (OPI) No. 162548/84) and the solution thus formed was stirred. Then, 20 g of triethylamine was added dropwise to the solution and the mixture was treated in the same manner as in Synthesis Example 1 to provide 36.5 g of Compound F as a powder.

(b) Synthesis of Coupler (18):

After dissolving 30 g of Compound F in 200 ml of a methanol solution of 10% KOH, the solution was stirred for 2 hours at room temperature. After the reaction was over, the reaction mixture was subjected to the post-treatment as in Synthesis Example 1 to provide 25 g of Coupler (18) as a powder.

| Elemental Analysis for $C_{39}H_{48}N_5O_5SCl$: | | | |
|---|---|---|---|
| | C | H | N |
| Calculated (%): | 63.78 | 6.59 | 9.54 |
| Found (%): | 63.62 | 6.61 | 9.55 |

The coupler for use in this invention may be added to a photographic material or a color developer. In the case of using the coupler in the photographic material, the addition amount of the coupler is $2 \times 10^{-3}$ mol to $5 \times 10^{-1}$ mol, preferably $1 \times 10^{-2}$ to $5 \times 10^{-1}$ mol, per mol of silver halide. In the case of the polymer coupler, the addition amount of the polymer coupler may be controlled so that the amount of the coloring moiety was as described above. In the case of using the coupler in a color developer, the amount thereof is 0.001 to 0.1 mol, preferably 0.01 to 0.05 mol, per 1,000 ml of the developer.

The coupler for use in this invention can be introduced in a silver halide emulsion layer by the method described in, for example, U.S. Pat. No. 2,322,027. For example, the coupler is dissolved in a high boiling organic solvent such as a phthalic acid alkyl ester (e.g., dibutyl phthalate, dioctyl phthalate, etc.), a phosphoric acid ester (e.g., diphenyl phosphate, triphenyl phosphate, tricresyl phosphate, dioctylbutyl phosphate, etc.), a citric acid ester (e.g., tributyl acetylcitrate, etc.), a benzoic acid ester (e.g., octyl benzoate, etc.), an alkylamide (e.g., dilaurylamide, etc.), a fatty acid ester (e.g., dibutoxyethyl succinate, diethyl azerate, etc.), a trimesic acid ester (e.g., tributyl trimesate, etc.), etc., or a low boiling organic solvent having a boiling point of about 30° C. to 150° C. such as a lower alkyl acetate such as ethyl acetate, butyl acetate, etc., ethyl propionate, secbutyl alcohol, methyl isobutyl ketone, β-ethoxyethyl acetate, methyl cellosolve acetate, etc., and then dispersed in a hydrophilic colloid solution as the solution. A mixture of the foregoing high boiling organic solvent and the low boiling organic solvent may be used for dissolving the coupler.

Also, a dispersion method using a polymer described in Japanese Patent Publication No. 39853/76 and Japanese Patent Application (OPI) No. 59943/76 can be used.

When the coupler has an acid group such as a carboxylic acid or sulfonic acid, the coupler is added to an aqueous solution of a hydrophilic colloid as an alkaline aqueous solution thereof.

As the binder or the protective colloid which is used for the silver halide emulsion layers, interlayers, etc., of the silver halide photographic materials for use in this invention, gelatin is advantageously used but other hydrophilic colloids may be used solely or together with gelatin.

In this invention, limed gelatin or acid-treated gelatin is used as gelatin. The preparation of such gelatin is described in detail in Arther Wise, *The Macromolecular Chemistry of Gelatin* (published by Academic Press, 1964).

As the foregoing hydrophilic colloids for use in this invention, there are various synthetic hydrophilic macromolecular materials, e.g., proteins such as gelatin derivatives, graft polymers of gelatin and other polymers, albumin, casein, etc.; cellulose derivatives such as hydroxyethyl cellulose, carboxymethyl cellulose, cellulose sulfuric acid ester, etc.; sugar derivatives such as sodium alginate, starch derivatives, etc.; and homopolymer or copolymers such as polyvinyl alcohol, polyvinyl alcohol partial acetal, poly-N-vinylpyrrolidone, polyacrylic acid, polymethacrylic acid, polyacrylamide, polyvinyl imidazole, polyvinyl pyrazole, etc.

For the photographic silver halide emulsion layers of the photographic materials for use in this invention, silver bromide, silver iodobromide, silver iodochlorobromide, silver chlorobromide, or silver chloride can be used as the silver halide. Silver iodobromide containing less than 15 mol % silver iodide is preferred. Silver iodobromide containing 2 mol % to 12 mol % silver iodide is particularly preferred.

There is no particular restriction on the mean grain size (in the case of spherical grains or grains similar to spherical grains, the grain size is the diameter of the grain and in the case of cubic grains, the grain size is the side length thereof and shown by the mean value based on the projected area) of silver halide grains in the photographic silver halide emulsions but the mean grain size of less than 3 microns is prefer- red.

The grain sizes may be narrow or broad. The silver halide grains in the photographic emulsions for use in this invention may have a regular crystal form such as a cube or an octahedron or an irregular crystal form such as a spherical form or a tabular form, or may be composed of a mixture of silver halide grains of various crystal forms.

Also, a silver halide emulsion wherein tabular silver halide grains having a diameter more than 5 times longer than the thickness thereof occupy more than 50% of the total projected area may be used in this invention. The silver halide grains may have a different phase between the inside thereof and the surface layer. Also, the silver halide grains forming latent images mainly on the surface thereof or in the inside thereof can be used.

The photographic silver halide emulsions for use in this invention can be prepared by the methods described in, for example, P. Glafkides, *Chimie et Physique Photographyque* (published by Paul Montel, 1967), G. F. Duffin, *Photographic Emulsion Chemistry* (published by The Focal Press, 1966), V.L. Zelikman et al., *Making and Coating Photographic Emulsion* (published by The Focal Press, 1964), etc.

That is, the photographic emulsions may be prepared by an acid process, a neutralization process, an ammonium process, etc. Also, as a system for reacting a soluble silver salt and a soluble halogen salt, a one side mixing process, a simultaneous mixing method, or a combination of these processes can be used.

Also, a process of forming silver halide grains in the presence of excessive silver ions (so-called reverse mixing process) can be used. As one system of the simultaneous mixing process, a so-called controlled double jet process that is a process wherein the pAg of the liquid phase for forming silver halide is kept at a constant value also can be used. According to this process, a silver halide emulsion containing silver halide of which the crystal form is regular and the grain sizes are almost uniform can be obtained.

Furthermore, two or more kinds of silver halide emulsions separately formed can be used as a mixture.

The formation or the physical ripening of silver halide grains can be performed in the presence of a cadmium salt, a zinc salt, a lead salt, a thallium salt, an iridium salt or the complex salt thereof, a rhodium salt or the complex salt thereof, an iron salt or the complex salt thereof, etc.

After the formation of a silver halide emulsion or physical ripening of the emulsion, soluble salts are usually removed and for the purpose, a so-called noodle washing process of performing the washing after gelling gelatin of the silver halide emulsion may be used or a flocculation process using an inorganic salt of a polyvalent anion, such as sodium sulfate, etc., an anionic surface active agent, an anionic polymer (e.g., polystyrenesulfonic acid), or a gelatin derivative (e.g., aliphatic acylated gelatin, aromatic acylated gelatin, aromatic carbamoylated gelatin, etc.) may be used.

The silver halide emulsions for use in this invention are usually chemically sensitized by a process such as the process described in, for example, H. Frieser, *Die Grundlagen der Photographischen Prozesse mit Silberhalogeniden, halogeniden,* 675-734 (published by Akademische Verlagsgesellschaft, 1968).

That is, a sulfur sensitization process using active gelatin or a compound containing sulfur capable of reacting with silver (e.g., a thiosulfate, a thiourea, a mercapto compound, a rhodanine, etc.); a reduction sensitization process using a reducing material (e.g., a stannous salt, an amine, a hydrazine derivative, formamidine sulfinate, a silane compound, etc.) and a noble metal sensitization process using a noble metal compound (e.g., a gold complex salt or a complex salt of a metal belonging to Group VIII of the Periodic Table, such as Pt, Ir, Pd, etc.) can be used solely or as a combination.

The silver halide photographic emulsions for use in this invention can further contain various compounds for preventing the occurrence of fog during the production or storage of the photographic materials or during photographic processing of the photographic materials or for stabilizing the photographic properties. Examples of these compounds are azoles such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (in particular, 1-phenyl-5-mercaptotetrazole), etc.; mercaptopyrimidines; mercaptotriazines; thioketo compounds such as oxazolinethione, etc.; azaindenes such as triazaindene, tetraazaindenes (in particular, 4-hydroxy-substituted (1,3,3a,7)tetraazaindenes), pentaazaindenes, etc.; benzenethiosulfonic acid, benzenesulfinic acid, benzenesulfonic acid amide, etc., which are known as antifoggants or stabilizers.

The silver halide photographic emulsion layers and/or other hydrophilic colloid layers of the photographic materials for use in this invention may further contain various surface active agents for various purposes such as as a coating aid, for static prevention, for the improvement of sliding properties, for the improvement of dispersibility of the emulsions, for adhesion prevention, and for the improvement of photographic characteristics (e.g., the acceleration of development, the increase of gradation, sensitization, etc.).

Examples of such surface active agents are nonionic surface active agents such as saponin (steroid system), alkylene derivatives (e.g., polyethylene glycol, polyethylene glycol/polypropylene glycol condensation product, polyethylene glycol alkyl ethers, polyethylene glycol alkylaryl ethers, polyethylene glycol esters, polyethylene glycol sorbitan esters, polyalkylene glycol alkyl amines or amides, polyethylene oxide addition products of silicone, etc.), glycidol derivatives (e.g., alkenylsuccinic acid polyglyceride, alkylphenol polyglyceride, etc.), fatty acid esters of polyhydric alcohols, alkyl esters of sugar, etc.; anionic surface active agents having an acid group such as a carboxy group, a sulfo group, a phospho group, a sulfuric acid ester group, a phosphoric acid ester group, etc., for example, alkylcarboxylates, alkylsulfonates, alkylbenzenesulfonates, alkylsulfuric acid esters, alkylphosphoric acid esters, N-acyl-N-alkyltaurines, sulfosuccinic acid esters, sulfoalkyl polyoxyethylene alkylphenyl ethers, polyoxyethylene alkylphosphoric acid esters, etc.; amphoteric surface active agents such as amino acids, aminoalkylsulfonic acids, aminoalkylsulfuric acid esters, aminoalkylphosphoric acid esters, alkylbetaines, amine oxides, etc.; and cationic surface active agents such as alkylamines, aliphatic or aromatic quaternary ammonium salts, heterocyclic quaternary ammonium salts such as pyridinium, imidazolium, etc., phosphonium salts or sulfonium salts having an aliphatic ring or a heterocyclic ring, etc.

The silver halide photographic emulsion layers of the photographic materials for use in this invention may contain polyalkylene oxide or the derivatives thereof (e.g., the ethers, esters, amines, etc., thereof), thioether compounds, thiomorpholines, quaternary ammonium salt compounds, urethane derivatives, urea derivatives, imidazole derivatives, 3-pyrazolidones, etc.

The photographic emulsion layers and other hydrophilic colloid layers of the photographic materials for use in this invention may further contain a dispersion of a water-insoluble or water sparingly soluble synthetic polymer for improving the dimensional stability. Examples of these polymer dispersions are polymers of alkyl (meth)acrylate, alkoxyalkyl (meth)acrylate, glycidyl (meth)acrylate, (meth)acrylamide, a vinyl ester (e.g., vinyl acetate), acrylonitrile, olefin, styrene, etc., solely or as a combination or as a combination of the foregoing monomer and acrylic acid, methacrylic acid, $\alpha,\beta$-unsaturated dicarboxylic acid, hydroxyalkyl (meth)acrylate, sulfoalkyl (meth)acrylate, styrenesulfonic acid, etc.

For the photographic processing of the photographic emulsion layers for use in this invention the known processes and known processing liquids described in, for example, Research Disclosure, No. 176, pages 28–30 can be applied. The processing temperature is usually selected in the range of 18° C. to 50° C. but the temperature may be, as the case may be, lower than 18° C. or higher than 50° C.

As a fix liquid, a fix composition generally used in the art can be used. As a fixing agent, a thiosulfate, a thiocyanate, as well as organic sulfur compounds which are known as fixing agents can be used. The fix liquid may contain a water-soluble aluminum salt as a hardening agent.

A color developer for use in this invention is generally composed of an alkaline aqueous solution of a color developing agent. Examples of the color developing agent are known aromatic primary amino developing agents such as, for example, phenylenediamines (e.g., 4-amino-N,N-diethylaniline, 3-methyl-4-amino-N,N-diethylaniline, 4-amino-N-ethyl-N-$\beta$-hydroxyethyl-aniline, 3-methyl-4-amino-N-ethyl-N-$\beta$-hydroxyethylaniline, 3-methyl-4-amino-N-ethyl-N-$\beta$-methanesulfonamidoethylaniline, 4-amino-3-methyl-N-ethyl-N-$\beta$-methoxyethylaniline, etc.), etc.

Other fixing agents described in L. F. A. Mason, Photographic Processing Chemistry (published by Focal Press, 1966), pages 226–229, U.S. Pat, Nos. 2,193,015 and 2,592,364, Japanese Patent Application (OPI) No. 64933/73, etc., may be used.

The color developer can further contain a pH buffer such as a sulfite, carbonate, borate, and phosphate of an alkaline metal and a development inhibitor and an antifoggant such as a bromide, an iodide, and organic antifoggants. Furthermore, the color developers may further contain, if necessary, a water softener, a preservative such as hydroxylamine, etc., an organic solvent such as benzyl alcohol, diethylene glycol, etc., a development accelerator such as polyethylene glycol, a quaternary ammonium salt, an amine, etc., a dye forming coupler, a competing coupler, a fogging agent such as sodium boron hydride, etc., an auxiliary developing agent such as 1-phenyl-3-pyrazolidone, etc., a tackifier, a polycarboxylic acid series chelating agent, an antioxidant, etc.

The photographic emulsion layers are usually bleached after color development. The bleach process may be performed simultaneously with the fixing process or may be performed separately. As the bleaching agent, the compound of a polyvalent metal such as iron (III), cobalt (III), chromium (VI), copper (II), etc., peracids, quinones, nitroso compounds, etc., can be used.

Examples of the bleaching agent are ferricyanides, dichromates, organic complex salts of iron (III) or cobalt (III); aminopolycarboxylic acids such as ethylenediaminetetraacetic acid, nitrilotriacetic acid, 1,3-diamino-2-propanoltetraacetic acid, etc.; complex salts of an organic acid such as citric acid, tartaric acid, malic acid, etc.; persulfates; permanganates; nitrosophenol, etc. Among these compounds, potassium ferricyanide, ethylenediaminetetraacetic acid iron (III) sodium salt, and ethylenediaminetetraacetic acid iron (III) ammonium salt are particularly preferred. The complex salt of ethylenediaminetetraacetic acid iron (III) may be used in a bleach liquid or a monobath blix liquid.

The photographic emulsions for use in this invention may be spectrally sensitized by methine dyes, etc. Dyes which are used in this invention include cyanine dyes, merocyanine dyes, complex cyanine dyes, complex merocyanine dyes, holopolar cyanine dyes, hemicyanine dyes, styryl dyes, and hemioxonol dyes. Particularly useful dyes are cyanine dyes, merocyanine dyes, and complex merocyanine dyes. For these dyes, any nuclei usually utilized for cyanine dyes as basic heterocyclic nuclei can be applied. That is, there are pyrroline nuclei, oxazoline nuclei, thiazoline nuclei, pyrrole nuclei, oxazole nuclei, thiazole nuclei, selenazole nuclei, imidazole nuclei, tetrazole nuclei, pyridine nuclei, etc.; nuclei formed by fusing an alicyclic hydrocarbon ring to the foregoing nuclei; and the nuclei formed by fusing an aromatic hydrocarbon ring to these nuclei such as indolenine nuclei, benzindolenine nuclei, indole nuclei, benzoxazole nuclei, naphthoxazole nuclei, benzothiazole nuclei, naphthothiazole nuclei, benzoselenazole nuclei, benzimidazole nuclei, quinoline nuclei, etc. These nuclei may be substituted on carbon atoms.

For merocyanine dyes or complex merocyanine dyes can be applied nuclei having a ketomethylene structure such as 5- or 6-membered heterocyclic nuclei, e.g., pyrazoline-5-one nuclei, thiohydantoin nuclei, 2-thioxazolidine-2,4-dione nuclei, thiazoline-2,4-dione nuclei, rhodanine nuclei, thiobarbituric acid nuclei, etc.

These sensitizing dyes may be used solely or as a combination. A combination of the sensitizing dyes is frequently used for the purpose of supersensiti- zation.

The photographic emulsions for use in this invention may further contain a dye which does not have a spectral sensitizing action by itself or a material which does not substantially absorb visible light but shows a supersensitizing action together with the foregoing sensitizing dye.

For example, there are aminostyryl compounds substituted by a nitrogen-containing heterocyclic group (shown ink, for example U.S. Pat. Nos. 2,033,390 and 3,635,721, etc.), aromatic organic acid/formaldehyde condensation products (shown in, for example, U.S. Pat. No. 3,743,510), cadmium salts, azaindene compounds, etc.

This invention can be applied to multilayer multicolor photographic materials having at least two photographic emulsion layers of different spectral sensitivities on a support.

A multilayer natural color photographic material ordinarily composed of a support having thereon at least one red-sensitive silver halide emulsion layer, at least one green-sensitive silver halide emulsion layer and at least one blue-sensitive silver halide emulsion layer. Usually the red-sensitive emulsion layer contains a cyan forming coupler, the green-sensitive emulsion layer contains a magenta forming coupler, and the blue-sensitive emulsion layer contains a yellow forming coupler, but as the case may be, different combinations may be employed.

The photographic material for use in this invention may contain, together with the coupler shown by the foregoing general formula (I), other dye forming couplers, that is, a compound capable of coloring by the oxidative coupling with an aromatic primary amino developing agent (e.g., a phenylenediamine derivative, an aminophenol derivative, etc.) in the same or different photographic silver halide emulsion layers or other non-light-sensitive layer or layers. Examples of such a dye forming couplers are as follows.

Examples of the magenta coupler are 5-pyrazolone couplers, pyrazolobenzimidazole couplers, pyrazoloimidazole couplers, pyrazolopyrazole couplers, pyrazolotriazole couplers, pyrazolotetrazole couplers, cyanoacetylcumarone couplers, chain closed acrylacetonitrile couplers, etc. Examples of the yellow coupler are acylacetamide couplers (e.g., benzoylacetanilides, pivaloylacetanilides, etc.). Also, examples of the cyan coupler are naphthol couplers, phenol couplers, etc. It is preferred that these couplers are nondiffusible couplers having a hydrophobic group called as a ballast group in the molecule or polymer type couplers.

The couplers may be 4-equivalent or 2-equivalent to silver ion. Also, the couplers may be colored couplers having a color correction effect or couplers releasing a development inhibitor with the development (so-called DIR couplers).

Also, the photographic materials may contain noncoloring DIR coupling compounds which form colorless products by coupling reactions and release development inhibitors in place of the DIR couplers. Furthermore, the photographic materials may contain a compound releasing a development inhibitor with the progress of development in place of the DIR coupler.

The couplers in this invention and the foregoing couplers can be incorporated in one silver halide emulsion layer as a combination of two or more kinds thereof for satisfying desired characteristics or the same coupler or compound may be incorporated in two or more layers.

The photographic materials for use in this invention may further contain an inorganic or organic hardening agent in the silver halide emulsion layers and other hydrophilic colloid layers. Examples of the hardening agent are chromium salts (e.g., chromium alum, chromium acetate, etc.), aldehydes (e.g., formaldehyde, glyoxal, glutaraldehyde, etc.), N-methylol compounds (e.g., dimethylolurea, methyloldimethyl hydantoin, etc.), dioxane derivatives (e.g., 2,3-dihydroxydioxane, etc.), active vinyl compounds (e.g., 1,3,5-triacryloylhexahydro- s-triazine, 1,3-vinylsulfonyl-2-propanol, etc.), active halogen compounds (e.g., 2,4-dichloro-6-hydroxy-s-triazine, etc.), mucohalogenic acids (e.g., mucochloric acid, mucophenoxychloric acid, etc.), etc. They can be used solely or as a combination.

When the photographic materials for use in this invention contain dyes or ultraviolet absorbents in the hydrophilic colloid layers, the layers may be mordanted by cationic polymers.

Also, the photographic materials for use in this invention may further contain hydroquinone derivatives, aminophenol derivatives, gallic acid derivatives, ascorbic acid derivatives, etc., as color fog preventing agents.

Examples of the ultraviolet absorbents which may be incorporated in the hydrophilic colloid layers of the photographic materials in this invention as described above are the aryl-substituted benzotriazole compounds (described in, for example, U.S. Pat. No. 3,533,794), the 4-thiazolidone compounds (described in, e.g., U.S. Pat. No. 3,314,794, 3,352,681), the benzophenone compounds (described in, for example, Japanese Patent Application (OPI) No. 2784/71), the cinnamic acid ester compounds (described in, for example, U.S. Pat. Nos. 3,705,805 and 3,707,375), the butadiene compounds (described in, for example, U.S. Pat. No. 4,045,229), and the benzoxazole compounds (described in, for example, U.S. Pat. No. 3,700,455).

Furthermore, ultraviolet absorptive couplers (e.g., α-naphtholic cyan dye forming couplers) and ultraviolet absorptive polymers may be used. The foregoing ultraviolet absorbents may be mordanted to specific layers.

The photographic materials for use in this invention may contain filter dyes in hydrophilic colloid layers or further contain water-soluble dyes in these layers for irradiation prevention or other various purposes. Such dyes include oxonol dyes, hemioxonol dyes, styryl dyes, merocyanine dyes, cyanine dyes, and azo dyes. Among these dyes, oxonol dyes, hemioxonol dyes, and merocyanine dyes are advantageous.

In the practice of this invention, the following known fading preventing agents or dye image stabilizers can be used solely or as a mixture. Examples of the fading preventing agent are hydroquinone derivatives, gallic acid derivatives, p-alkoxyphenols, p-oxyphenol derivatives, and bisphenols.

The invention will further be illustrated in and by the following examples which are not meant to be limiting.

Unless otherwise indicated, all percents, ratios, etc., are by weight.

, EXAMPLE 1

Film A

In 15 ml of tricresyl phosphate and 10 ml of ethyl acetate was dissolved 10.7 g ($1.25 \times 10^{-2}$ mol) of Compound (1) of this invention under heating and after adding 100 g of an aqueous 10% gelatin solution containing alkylnaphthalene sulfonate to the solution and the resultant mixture was stirred by means of a homogenizer to provide an emulsion. The emulsion was mixed with 300 g (13.5 g of silver) of a green-sensitive silver chlorobromide emulsion (45% Br and 55% Cl) and after adding thereto sodium dodecylbenzenesulfonate as a coating aid and 2-hydroxy-4,6-dichloro-s-triazine as a hardening agent, the mixture thus obtained was coated on a baryta coated support at a silver coverage of 700 mg/m² and further a gelatin layer was coated thereon (1 g/m² of gelatin) to provide Sample Film A.

Films B to I

By following the same procedure as the preparation of Film A using each of Compounds (4), (6), (18), (23), (27), (33), (35) and (44) of this invention in place of Compound (1), Films B to I were prepared.

Comparison Films Y and Z

By following the same procedure as the preparation of Film A except that each of following Comparison Compounds Y ans Z was used in place of Compound (1) of this invention, Films Y and Z are prepared.

Comparison Compound Y

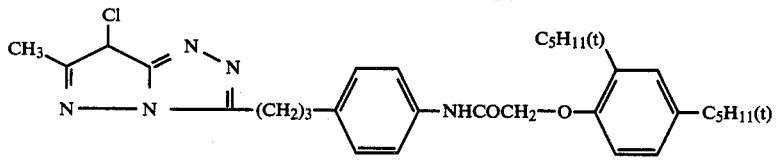

Comparison Compound Z

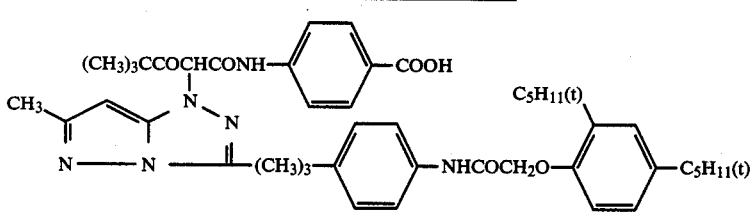

Each of the sample films thus prepared was light-exposed for 1 second using an actinometer at 1,000 lux and processed as follows.

| Processing Step | Temperature (°C.) | Time |
|---|---|---|
| Development | 33 | 3 min |
| Blix | 33 | 1 min 30 sec |
| Wash | 28-35 | 3 min |
| Drying | | |

The compositions of the processing liquids used in the above processing steps were as follows.

| Developer | |
|---|---|
| Benzyl Alcohol | 15 ml |
| Na₂SO₃ | 5 g |
| KBr | 0.4 g |
| Hydroxyl Sulfate | 2 g |

| -continued | |
|---|---|
| 4-Amino-3-methyl-N—ethyl-N—β-(methanesulfonamido)ethyl-p-phenylenediamine | 6 g |
| Na₃CO₃ (monohydrate) | 30 g |
| Water added to make | 1 liter |
| | (pH 10.1) |
| Blix Liquid | |
| Ammonium Thiosulfate (70% wt %) | 150 ml |
| Na₂SO₃ | 15 g |
| Ethylenediaminetetraacetic Acid Sodium Iron Salt | 40 g |
| Ethylenediaminetetraacetic Acid | 4 g |
| Water to make | 1 liter |
| | (pH 6.9) |

After processing, the dye maximum density was measured about each film thus processed using a Macbeth densitometer and status A filter, Also, after processing, each filjm thus processed was irraidated by light using a fluorescent light fade-o-meter to perform a fading test (15,000 lux, 4 weeks). The maximum densities and the residual densities after the fading test of the film sjamples of this invention and Comparison Samples Y and Z are shown in the following table.

| Film Sample | Compound | Maximum Density | Residual Density after Fading |
|---|---|---|---|
| Y | Comparison Compound Y | 1.71 | 0.34 |
| Z | Comparison Compound Z | 1.90 | 0.38 |
| A | Compound (1) | 2.09 | 1.67 |
| B | Compound (4) | 2.28 | 1.82 |
| C | Compound (6) | 2.19 | 1.64 |
| D | Compound (18) | 2.19 | 1.31 |
| E | Compound (23) | 2.30 | 1.50 |
| F | Compound (27) | 2.40 | 1.92 |
| G | Compound (33) | 2.45 | 1.83 |
| H | Compound (35) | 2.28 | 1.25 |
| I | Compound (44) | 2.35 | 1.41 |

As shown in the above results, the samples of this invention using the compounds of this invention show high coloring density and further have very excellent light fastness as compared to the comparison samples using Comparison Compounds Y and Z.

EXAMPLE 2

A multilayer color photographic material was prepared by forming, in succession, the following layers on a polyethylene terephthalate film support.

First Layer: Antihalation Layer
A gelatin layer containing black colloid silver.

Second Layer: Interlayer
A gfelatin layer containing an emulsified dispersion of 2,5-di-t-octylhydroquinone.

Third Layer: First Red-Sensitive Emulsion Layer

| Silver iodobromide emulsion (silver iodide: 5 mol %) silver coverage 1.6 g/m² | |
|---|---|
| Sensitizing Dye I | $4.5 \times 10^{-4}$ mol per mol of silver |
| Sensitizing Dye II | $1.5 \times 10^{-4}$ mol per mol of silver |
| Coupler EX-1 | 0.04 mol per mol of silver |
| Coupler EX-3 | 0.003 mol per mol of silver |
| Coupler EX-6 | 0.0006 mol per mol of silver |

Fourth Layer: Second Red-Sensitive Emulsion Layer

| Silver iodobromide emulsion (silver iodide: 10 mol %) Silver coverage 1.4 g/m² | |
|---|---|
| Sensitizing Dye I | $3 \times 10^{-4}$ mol per mol of silver |
| Sensitizing Dye II | $1 \times 10^{-4}$ mol per mol of silver |
| Coupler EX-1 | 0.002 mol per mol of silver |
| Coupler EX-2 | 0.02 mol per mol of silver |
| Coupler EX-3 | 0.0016 mol per mol of silver |

Fifth Layer: INterlayer
Same as the second layer.

Sixth Layer: First Green-Sensitive Emulsion Layer

| Silver iodobromide emulsion (silver iodide: 4 mol %) Silver coverage 1.2 g/m² | |
|---|---|
| Sensitizing Dye III | $5 \times 10^{-4}$ mol per mol of silver |
| Sensitizing Dye IV | $2 \times 10^{-4}$ mol per mol of silver |
| Compound (1) of this invention | 0.05 mol per mol of silver |
| Coupler EX-4 | 0.008 mol per mol of silver |
| Coupler EX-6 | 0.0015 mol per mol of silver |

Seventh Layer: Second Green-Sensitive Emulsion Layer

| Silver iodobromide emulsion (silver iodide: 8 mol %) Silver coverage 1.3 g/m² | |
|---|---|
| Sensitizing Dye III | $3 \times 10^{-4}$ mol per mol of silver |
| Sensitizing Dye IV | $1.2 \times 10^{-4}$ mol per mol of silver |
| Compound (4) of this invention | 0.02 mol per mol of silver |
| Coupler EX-7 | 0.0003 mol per mol of silver |

Eighth Layer: Yellow Filter Layer
A gelatin layer containing an emulsified dispersion of yellow colloid silver and 2,5-di-t-octylhydroquinone in an aqueous gelatin solution.

Ninth Layer: First Blue-Sensitive Emulsion Layer

| Silver iodobromide emulsion (silver iodide: 6 mol %) Silver coverage 0.7 g/m² | |
|---|---|
| Coupler EX-5 | 0.25 mol per mol of silver |
| Coupler EX-6 | 0.015 mol per mol of silver |

Tenth Layer: Second Blue-Sensitive Emulsion Layer

| Silver iodobromide emulsion (silver iodide: 6 mol %) Silver coverage 0.6 g/m² | |
|---|---|
| Coupler EX-5 | 0.06 mol per mol of silver |

Eleventh Layer: First Protective Layer
Silver iodobromide emulsion (silver iodide: 1 mole % mean grain size 0.07µ) Silver coverage 0.5 g/m²
A gelatin layer containing the silver halide emulsion and an emulsified dispersion of Ultraviolet Absorbent UV-1.

Twelfth Layer: Second Protective Layer
A gelatin layer containing polymethyl methacrylate particles (diameter: about 1.5µ).

Each of the aforesaid layers further contained Gelatin Hardening Agent H-1 and a surface active agent. Thus, Sample 101 was prepared.

The compounds used for making the sample are shown below.

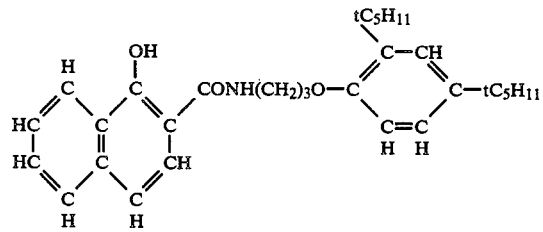

Coupler EX-1

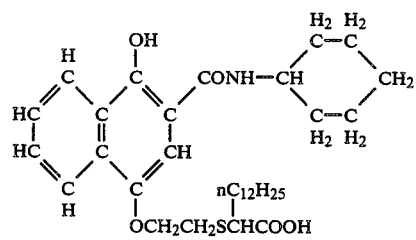

EX-2

-continued
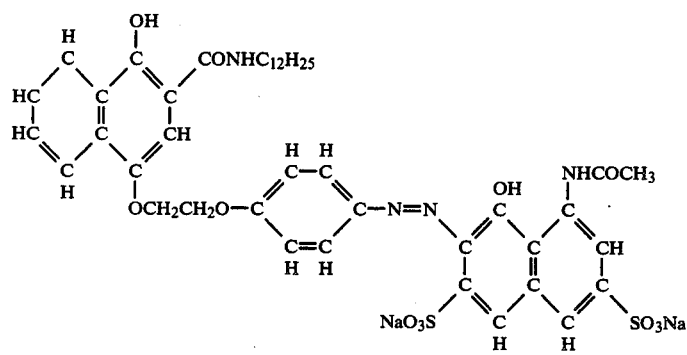
EX-3
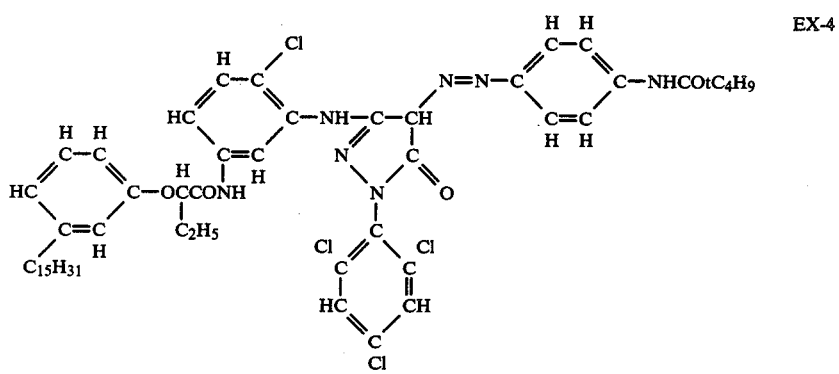
EX-4
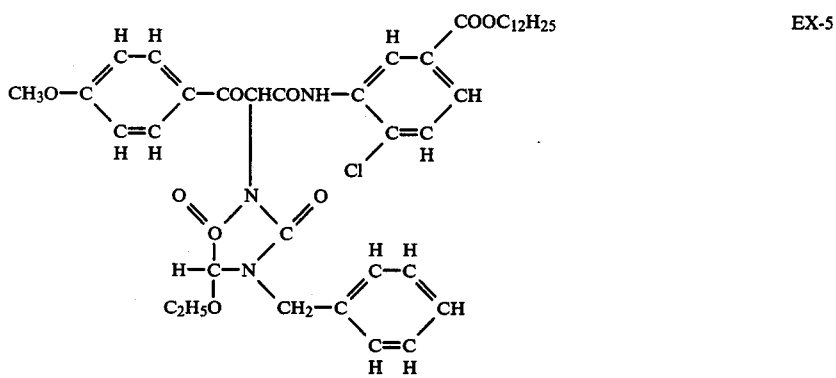
EX-5
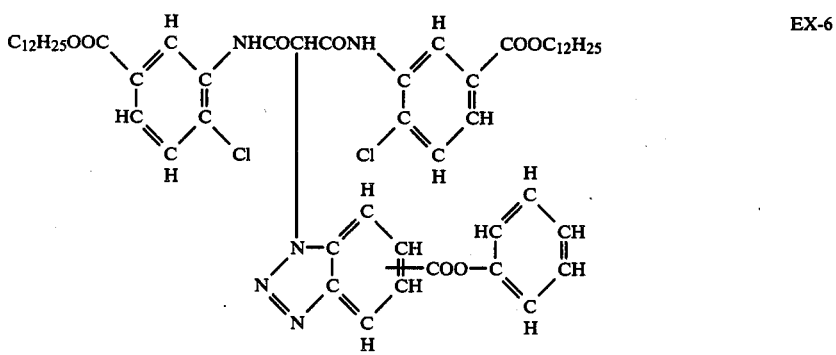
EX-6

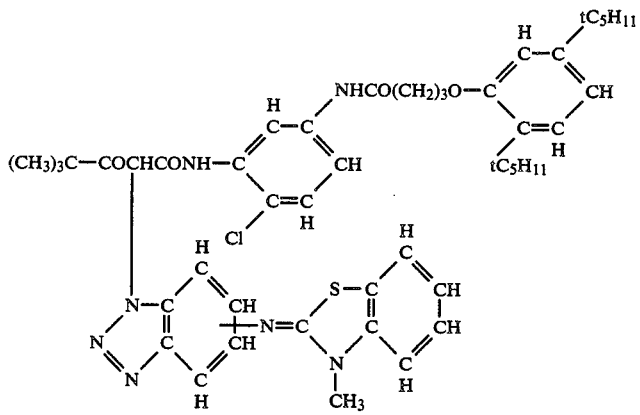
EX-7
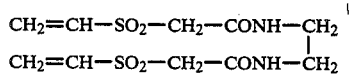
H-1
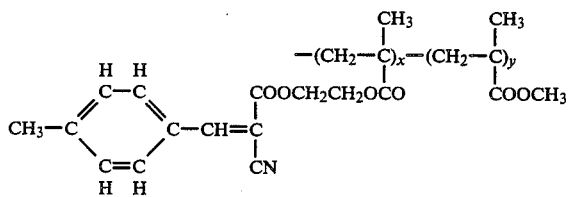
UV-1
x/y = 7/3 (weight ratio)
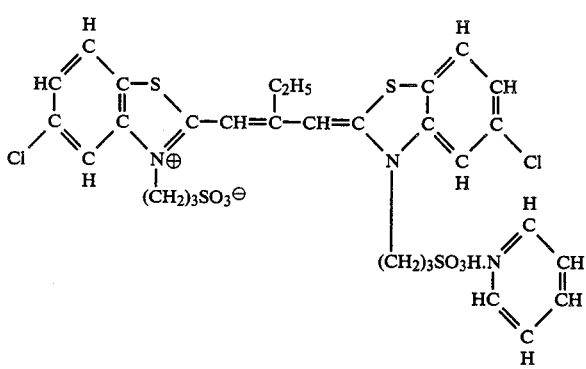
Sensitizing Dye I
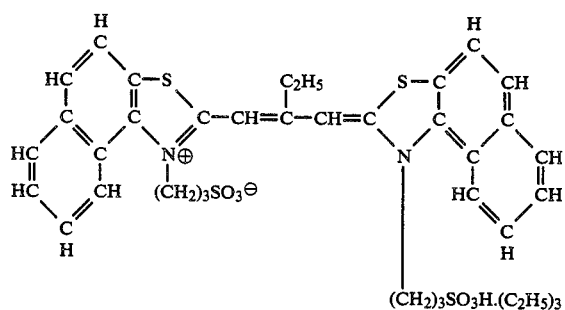
Sensitizing Dye II -continued

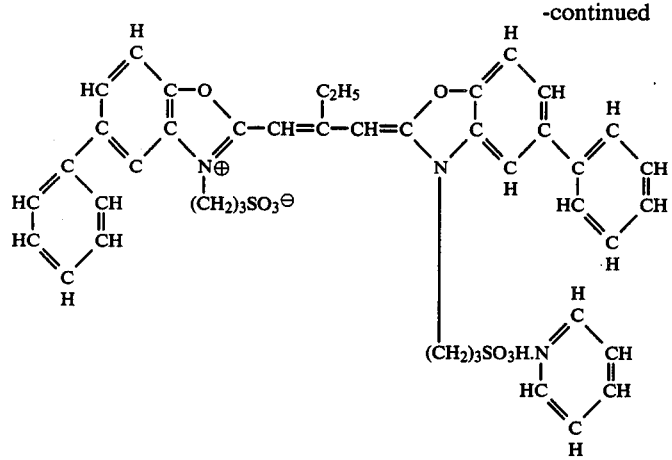

Sensitizing Dye III

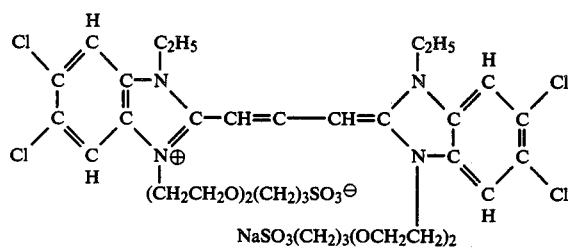

Sensitizing Dye IV

The sample was exposed as in Example 1 and processed as follows.

| 1. Color Development | 3 min 15 sec |
|---|---|
| 2. Bleach | 6 min 30 sec |
| 3. Wash | 3 min 15 sec |
| 4. Fix | 6 min 30 sec |
| 5. Wash | 3 min 15 sec |
| 6. Stabilization | 3 min 15 sec |

The compositions of the processing liquids used for the above processing steps were as follows.

| Color Developer | |
|---|---|
| Sodium Nitrilotriacetate | 1.0 g |
| Sodium Sulfite | 4.0 g |
| Sodium Carbonate | 30.0 g |
| Potassium Bromide | 1.4 g |
| Hydroxylamine Sulfate | 2.4 g |
| 4-(N—Ethyl-N—β-hydroxyethylamino)-2-methylaniline Sulfate | 4.5 g |
| Water to make | 1 liter |
| Bleach Liquid | |
| Ammonium Bromide | 160.0 g |
| Aqueous Ammonia (28%) | 25.0 ml |
| Ethylenediaminetetraacetic Acid Sodium Iron Salt | 130.0 g |
| Glacial Acetic Acid | 14.0 ml |
| Water to make | 1 liter |
| Fix Liquid | |
| Sodium Tetrapolyphosphate | 2.0 g |
| Sodium Sulfite | 4.0 g |
| Sodium Hydrogensulfite | 4.6 g |
| Water to make | 1 liter |
| Stabilization Liquid | |
| Formalin | 8.0 ml |
| Water to make | 1 liter |

It was confirmed that the color photographic material (Sample 101) using the compound in this invention was excellent in shelf life and showed less change of coloring density when the photographic material was developed after exposing it to formalin vapor. When the photographic material was image-exposed, developed and printed on a color paper, a color print having a beautiful color image was obtained.

While the invention has been described in detail and with reference to specific embodiments thereof, it will be apparent to one skilled in the art that various changes and modifications can be made therein without departing from the spirit and scope thereof.

What is claimed is:

1. A color image forming process which comprises developing a silver halide photographic material using an armatic primary amino developing agent in the presence of a blocked magenta dye forming coupler represented by the following general formula (I):

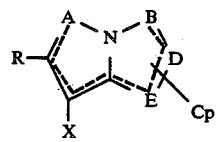 (I)

wherein R represents a hydrogen atom or a substituent; X represents a hydrogen atom, a halogen atom, a carboxy group or a coupling releasable group; Cp represents a coupling block group capable of forming a colorless or alkali-soluble product by reaction with the oxidation product of a color developing agent; A represents

when Cp is bonded and —N= when Cp is not bonded; B and E each represents

when Cp is bonded and —N= or

when Cp is not bonded; D represents —N= or

(wherein R has the same significance as defined above and said Rs in said D and B and E may be the same or different); and≡≡≡represents three movable double bonds; said Cp is not, however, bonded to E when A, D and E simultaneously contain a nitrogen atom and B contains a carbon atom; said coupler may form a dimer or more oligomers at R or X; and said substituent Rs on adjacent carbon atoms may form a ring with each other.

2. A color image forming process as claimed in claim 1, wherein the compound of the general formula (I) is one member selected from the group consisting of general formulae (II), (III) and (IV) as shown below:

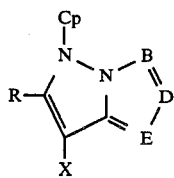 (II)

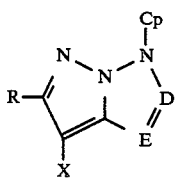 (III)

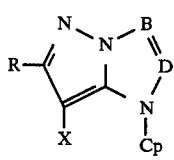 (IV)

wherein R, X, B, D, E and Cp in general formulae (II), (III) and (IV) are the same as defined in general formula (I), provided that in general formula (IV) the case wherein D is —N= when B is

is excluded.

3. A color image forming process as claimed in claim 1, wherein the coupler of the general formula (I) exists at the side chain of a polymer as a coupler group.

4. A color image forming process as claimed in claim 3, wherein said polymer is induced from a vinyl monomer having the moiety shown by general formula (I) and at least one of R and X represents a vinyl-containing group.

5. A color image forming process as claimed in claim 1, wherein Cp is one member selected from the group consisting of the following general formulae (V), (VI), (VII), (VIII) and (IX) as follows:

 (V)

wherein $R_2$ represents an alkoxycarbonyl group, an aryloxycarbonyl group, a heterocyclic oxycarbonyl group, an alkylcarbamoyl group, an arylcarbamoyl group, a heterocyclic carbamoyl group, an alkylcarbonyl group, an arylcarbonyl group, a heterocyclic carbonyl group, an alkoxythiocarbonyl group, an aryloxythiocarbonyl group, an alkylsulfonyl group, an arylsulfonyl group, a heterocyclic sulfonyl group, an alkylsulfinyl group, an arylsulfinyl group, a heterocyclic sulfinyl group, an alkylsulfamoyl group, an arylsulfamoyl group, a heterocyclic sulfamoyl group, a nitro group, a cyano group, or a carboxy group and $R_3$ represents, in addition to the group as defined for $R_2$, a hydrogen atom, a halogen atom, an alkyl group, an aryl group, an alkoxy group, an aryloxy group, an alkylthio group, an arylthio group, an acyloxy group, an amino group, an alkylcarbamoyl group, an arylcarbamoyl group, an acylcarbamoyl group, or a heterocyclic ring; and $R_1$, $R_2$ may cyclize with each other to form a 5- or 6-membered hydrocarbon ring or a 5- or 6-membered heterocyclic ring having a carbonyl group at the α-position to

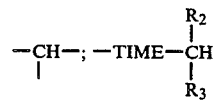 (VI)

wherein $R_2$ and $R_3$ have the same meaning as stated for general formula (V) and TIME represents a group that causes an intramolecular nucleophilic reaction after releasing the group -TIME⊖ by the reaction of

and the oxidation product of a color developing agent or a group that causes electron migration along a covalent system;

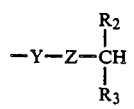 (VII)

wherein $R_2$ and $R_3$ have the same meaning as defined for the general formula (V), Y represents an oxygen atom or a sulfur atom and Z represents a carbonyl group, a thiocarbonyl group, an oxalyl group, a sulfonyl group, a sulfinyl group, a methylene group or a substituted methylene group;

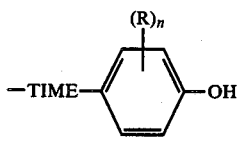

(VIII)

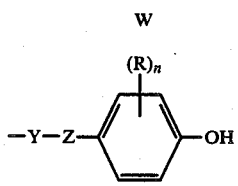

(IX)

wherein

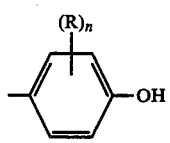

W represents a cyan dye forming coupler residue having a phenol nucleus or naphthol nucleus, W represents an atomic group forming a naphthol nucleus by causing condensation with a phenol nucleus, R has the same meaning as defined in formula (V), n represents an integer of 1 to 4 when the foregoing cyan dye forming coupler has a phenol nucleus or an integer of 1 to 6 when the coupler has a naphthol nucleus, TIME has the same meaning as defined in general formula (VI) and -Y-Z- has the same meaning as defined for general formula (VII), provided that when n is 2 or more, Rs may be the same or different.

6. A color image forming process as claimed in claim 1, wherein the compound of the general formula (I) is present in the silver halide photographic material in an amount of $2 \times 10^{-3}$ mol to $5 \times 10^{-1}$ mol per mol of silver halide.

7. A color image forming process as claimed in claim 1, wherein the compound of the general formula (I) is present in a color developer in an amount of 0.001 to 0.1 mol per 1,000 ml of the color developer.

8. A color image forming process as claimed in claim 1, wherein the substituent for R represents a halogen atom, a substituted or unsubstituted alkyl group, a substituted or unsubstituted aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imido group, a sulfamoylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, or an aryloxycarbonyl group.

9. A color image forming process as claimed in claim 1, wherein the compound of the general formula (I) forms a bis compound via R, and R is a divalent group selected from the group consisting of a substituted or unsubstituted alkylene group, a substituted or unsubstituted phenylene group, —NHCO—$R_5$—CONH— and —S—$R_6$—S—, where $R_5$ represents a substituted or unsubstituted alkylene or phenylene group and $R_6$ represents a substituted or unsubstituted alkylene group.

10. A color image forming process as claimed in claim 1, wherein the compound of the general formula (I) forms a bis compound via X, and X is a divalent group formed from a monovalent group selected from a group bonded through an oxygen atom, a group bonded through a nitrogen atom, and a group bonded through a sulfur atom.

11. A color image forming process as claimed in claim 1, wherein the compound of the general formula (I) forms an oligomer via R or X, and at least one of R and X represents a vinyl-containing group.

12. A color image forming process as claimed in claim 1, wherein the compound of the general formula (I) forms a copolymer via R or X with a non-coloring ethylenic monomer, and at least one of R and X represents a vinyl-containing group.

* * * * *